(12) United States Patent
Wertz et al.

(10) Patent No.: US 10,889,901 B2
(45) Date of Patent: Jan. 12, 2021

(54) ULTRAVIOLET-STABILIZED CORROSION INHIBITORS

(71) Applicant: International Business Machines Corporation, Armonk, NY (US)

(72) Inventors: Jason T. Wertz, Pleasant Valley, NY (US); Brandon M. Kobilka, Tucson, AZ (US); Joseph Kuczynski, North Port, FL (US); Jacob T. Porter, Highland, NY (US)

(73) Assignee: International Business Machines Corporation, Armonk, NY (US)

( * ) Notice: Subject to any disclaimer, the term of this patent is extended or adjusted under 35 U.S.C. 154(b) by 21 days.

(21) Appl. No.: 16/044,692

(22) Filed: Jul. 25, 2018

(65) Prior Publication Data

US 2020/0032401 A1 Jan. 30, 2020

(51) Int. Cl.
| | | |
|---|---|---|
| *C23F 11/12* | (2006.01) | |
| *C23F 11/14* | (2006.01) | |
| *C23F 11/16* | (2006.01) | |
| *G03F 7/004* | (2006.01) | |
| *C07D 277/82* | (2006.01) | |

(Continued)

(52) U.S. Cl.
CPC .......... *C23F 11/149* (2013.01); *C07D 249/18* (2013.01); *C07D 263/58* (2013.01); *C07D 277/82* (2013.01); *C23F 11/12* (2013.01); *C23F 11/165* (2013.01); *G03F 7/0045* (2013.01)

(58) Field of Classification Search
CPC ....... C23F 11/12; C23F 11/149; C23F 11/165; G03F 7/0045; C07D 249/18; C07D 263/58; C07D 277/82
See application file for complete search history.

(56) References Cited

U.S. PATENT DOCUMENTS

| | | |
|---|---|---|
| 4,129,521 A | 12/1978 | Strobel |
| 4,438,190 A | 3/1984 | Ishimaru et al. |

(Continued)

FOREIGN PATENT DOCUMENTS

| | | |
|---|---|---|
| CN | 101029031 A | 9/2007 |
| WO | 200242281 A1 | 5/2002 |

OTHER PUBLICATIONS

Yulong Gong, Zhenqiang Wang, Fang Gao, Shengtao Zhang, and Hongru Li, Synthesis of New Benzotriazole Derivatives Containing Carbon Chains as the Corrosion Inhibitors for Copper in Sodium Chloride Solution, Ind. Eng. Chem. Res. 2015, 54, 12242-12253 (Year: 2015).*

(Continued)

*Primary Examiner* — Bijan Ahvazi
(74) *Attorney, Agent, or Firm* — Patterson + Sheridan, LLP

(57) ABSTRACT

According to one embodiment of the present disclosure, a method of forming an ultraviolet-stabilized corrosion inhibitor is provided. The method includes forming a functionalized azole; forming a functionalized photosensitizer; and forming an ultraviolet-stabilized corrosion inhibitor by reacting the functionalized azole with the functionalized photosensitizer. In another embodiment, an ultraviolet-stabilized corrosion inhibitor is provided. The inhibitor includes an azole bonded to a photosensitizer. In another embodiment, an article of manufacture is provided. The article of manufacture includes a material comprising a reaction product of an azole and a photosensitizer.

19 Claims, 10 Drawing Sheets

(51) Int. Cl.
*C07D 263/58* (2006.01)
*C07D 249/18* (2006.01)

(56) References Cited

U.S. PATENT DOCUMENTS

| | | |
|---|---|---|
| 5,069,805 A | 12/1991 | Braig et al. |
| 6,515,051 B2 | 2/2003 | Ravichandran et al. |
| 9,907,736 B1 | 3/2018 | King et al. |
| 2007/0003860 A1* | 1/2007 | Takeda ............... G03F 7/085 430/270.1 |

OTHER PUBLICATIONS

Yulong Gong, Zhenqiang Wang, Shengtao Zhang, Ziping Luo, Fang Gao, and Hongru Li, New ESIPT-Inspired Photostabilizers of Two-Photon Absorption Coumarin-Benzotriazole Dyads: From Experiments to Molecular Modeling, Ind. Eng. Chem. Res. 2016, 55, 5223-5230 (Year: 2016).*

Borowska et al., "Oxidation of benzotriazole and benzothiazole in photochemical processes: Kinetics and formation of transformation products," Chemical Engineering Journal 304 (2016) 852-863.

* cited by examiner

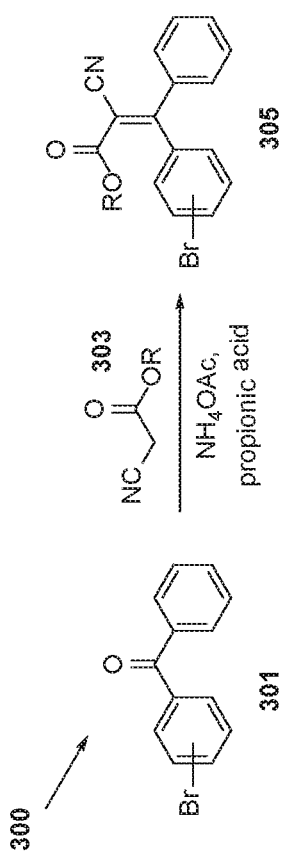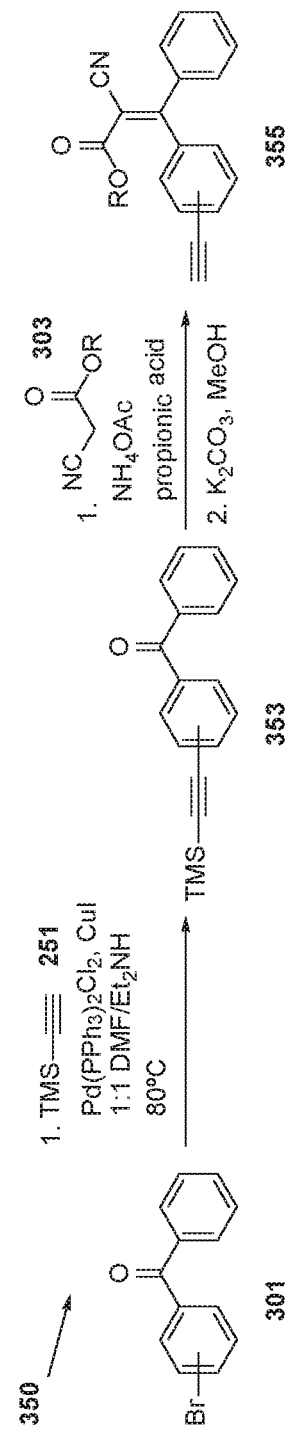
FIG. 3A
FIG. 3B

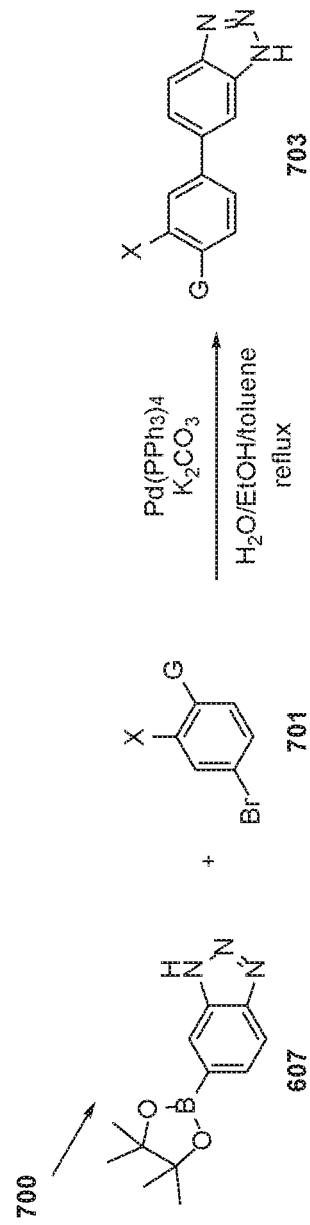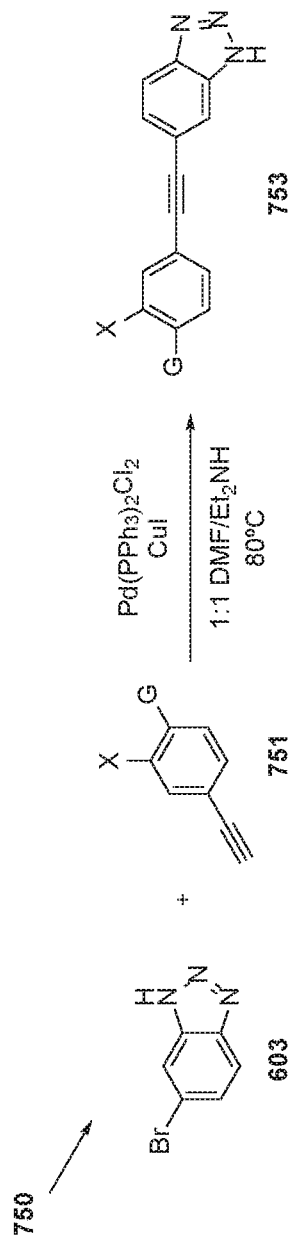
FIG. 7A
FIG. 7B

ULTRAVIOLET-STABILIZED CORROSION INHIBITORS

BACKGROUND

The present disclosure relates to corrosion inhibitors and, more specifically, to ultraviolet-stabilized corrosion inhibitors.

Copper and copper alloys (e.g., brass and bronze) are widely used in industry due to favorable properties such as high electrical and thermal conductivity and have applications in the production of wires, sheets, tubes, and water cooling systems in various industries including the electronics industries. However, copper and copper alloys are susceptible to corrosion, e.g., pitting corrosion. The formation of corrosion products negatively impacts the performance of systems having copper components.

Corrosion inhibitors, e.g., azoles, have been employed when copper and copper alloys are used in corrosive environments. However, azoles (e.g., benzotriazole) become degraded by photochemical processes. For example, when exposed to ultraviolet (UV) light, azoles no longer protect copper from corrosion.

Therefore, there is a need for compounds that retain good corrosion inhibitory properties after exposure to light.

SUMMARY

According to one embodiment of the present disclosure, a method of forming an ultraviolet-stabilized corrosion inhibitor is provided. The method includes forming a functionalized azole; forming a functionalized photosensitizer; and forming an ultraviolet-stabilized corrosion inhibitor by reacting the functionalized azole with the functionalized photosensitizer.

In another embodiment, an ultraviolet-stabilized corrosion inhibitor is provided. The inhibitor includes an azole bonded to a photosensitizer.

In another embodiment, an article of manufacture is provided. The article of manufacture includes a material comprising a reaction product of an azole and a photosensitizer.

BRIEF DESCRIPTION OF THE SEVERAL VIEWS OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 3A is a chemical reaction diagram of a method 300 of forming a photosensitizer according to some embodiments.

FIG. 3B is a chemical reaction diagram of a method 350 of forming a photosensitizer according to some embodiments.

FIG. 7A is a chemical reaction diagram of a method 700 of forming an ultraviolet-stabilized corrosion inhibitor according to some embodiments.

FIG. 7B is a chemical reaction diagram of a method 750 of forming an ultraviolet-stabilized corrosion inhibitor according to some embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1A:
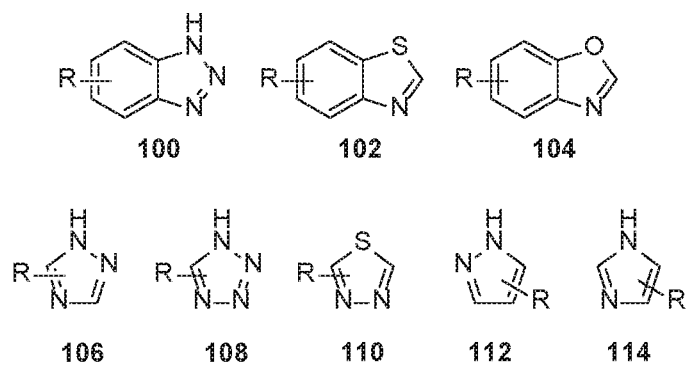
FIG. 1A shows examples of azoles useful for embodiments described herein.

Embodiments described herein illustrate corrosion inhibitors, and methods of forming such, having a reduced (or eliminated) ability to undergo degradation when exposed to light (e.g., UV light). The methods and materials described herein find use in a wide variety of applications such as liquid cooling circuits.

Liquid cooling, e.g., water cooling, is a method of heat removal commonly used for cooling components in petroleum refineries, chemical plants, internal combustion engines, and power plants. Water cooling can also be used to cool various components inside computers such as CPUs, hard disk drives, motherboards, and power supplies. By transferring the heat away from hot computer components, the components show improved performance.

In certain circumstances, UV light treatment is used to sterilize the water solution used to cool the components. In order to maintain a high water quality of the water solution, the UV light treatment can be continuous within the cooling loop to prevent bacteria growth. Because most conventional systems that include water treatment are not hermetic, there is a need to continuously treat and maintain high water quality. The water solution contains various components including corrosion inhibitors (e.g., azoles). However, the azoles degrade upon exposure to UV light, and after a short period of exposure the azole no longer protects the copper components from corrosion. Thus, embodiments of the present disclosure advantageously include corrosion inhibitors, e.g., azoles, modified with photosensitizers. The photosensitizers act to protect the azole portion of the molecule from undergoing photodegradation due to exposure to UV light.

This disclosure includes chemical structures that show atomic compositions of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals interactions, isoelectronic structures, and the like may vary among instances of the same chemical compound. Additionally, unless otherwise noted, the disclosed structures cover all stereoisomers, conformers, rotamers, isomers, and enantiomers of the represented compounds.

Numbered chemical structures are numbered using numbers, or numbers and letters, in parentheses. Unless otherwise noted, chemical reactions are performed at ambient conditions or under slight heating with no special atmosphere or head space, and may be performed using standard organic solvents to manage mix properties such as viscosity and flow index. Standard procedures for quenching the reaction, solvent removal, and purification are performed.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s).

As used herein, the term "substituted" refers to a hydrogen group that has been replaced with a carbon atom, a heteroatom, or a heteroatom-containing group. For example, a "substituted hydrocarbyl" is a radical made of carbon and hydrogen where at least one hydrogen is replaced by a carbon atom, a heteroatom, or heteroatom-containing group.

The term "carbon substituted" refers to a substituted species where a hydrogen group has been replaced with a carbon atom.

The term "heterosubstituted" refers to a substituted species where a hydrogen group has been replaced with a heteroatom or heteroatom-containing group.

The following abbreviations may be used herein: TMS is trimethylsilyl, DMF (also referred to as dmf) is dimethylformamide, MeOH is methanol, EtOH is ethanol, Me is methyl, Et is ethyl, Pr is propyl, cPr is cyclopropyl, nPr is normal propyl, iPr is isopropyl, Bu is butyl, nBu is normal butyl, iBu is isobutyl, sBu is sec-butyl, tBu is tert-butyl, p-tBu is para-tert-butyl, Ph is phenyl, Bn is benzyl (i.e., $CH_2Ph$), Oct is octyl, Cy is cyclohexyl, p-Me is para-methyl, THF (also referred to as thf) is tetrahydrofuran, tol is toluene, and EtOAc is ethyl acetate.

Room temperature is between about 15° C. and 25° C. unless otherwise indicated.

As used herein, "alkoxy" includes those where the alkyl group is a $C_1$ to $C_{10}$ hydrocarbyl. The alkyl group may be straight chain, branched, or cyclic. The alkyl group may be saturated or unsaturated. In some embodiments, the alkyl group may include at least one aromatic group.

The terms "alkyl group," "alkyl radical," "alkyl," "hydrocarbyl radical," "hydrocarbyl," and "hydrocarbyl group" are used interchangeably throughout this document. Likewise, the terms "group," "radical," and "substituent" are also used interchangeably in this document. For purposes of this disclosure, "alkyl group" refers to $C_1$-$C_{100}$ radicals, that may be linear, branched, or cyclic, and when cyclic, aromatic or non-aromatic. Examples of such radicals include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and their substituted analogues. Substituted alkyl radicals are those in which at least one hydrogen atom of the hydrocarbyl radical has been substituted with at least one halogen (such as Br, Cl, F or I) or at least one functional group such as $C(O)R^*$, $C(O)NR^*_2$, $C(O)OR^*$, $NR^*_2$, $OR^*$, $SeR^*$, $TeR^*$, $PR^*_2$, $AsR^*_2$, $SbR^*_2$, $SR^*$, $BR^*_2$, $SiR^*_3$, $GeR^*_3$, $SnR^*_3$, and $PbR^*_3$ (where $R^*$ is independently a hydrogen or hydrocarbyl radical, and two or more $R^*$ may join together to form a substituted or unsubstituted saturated, partially unsaturated or aromatic cyclic or polycyclic ring structure), or where at least one heteroatom has been inserted within a hydrocarbyl ring.

The term "alkenyl" or "alkenyl group" or "alkenyl radical" refers to a straight-chain, branched-chain, or cyclic hydrocarbon radical having one or more double bonds. These alkenyl radicals may be optionally substituted. Examples of suitable alkenyl radicals include ethenyl, propenyl, allyl, 1,4-butadienyl cyclopropenyl, cyclobutenyl, cyclopentenyl, cyclohexenyl, cyclooctenyl, including their substituted analogues.

The term "alkoxy" or "alkoxy group" or "alkoxy radical" refers to a radical with an oxygen atom bonded to an organic group (e.g., an alkyl or aryl group) wherein the term alkyl is as defined above. Examples of alkoxy radicals include methoxy, ethoxy, n-propoxy, iso-propoxy, n-butoxy, iso-butoxy, sec-butoxy, tert-butoxy, and phenoxyl.

The term "aryl" or "aryl group" or "aryl radical" includes a $C_4$-$C_{20}$ aromatic ring, such as a six carbon aromatic ring, and substituted variants thereof, including phenyl, 2-methylphenyl, xylyl, and 4-bromo-xylyl. Likewise, heteroaryl refers to an aryl group where a ring carbon atom (or two or three ring carbon atoms) has been replaced with a heteroatom, preferably N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

Where isomers of a named alkyl, alkenyl, alkoxy, or aryl group exist (e.g., n-butyl, iso-butyl, sec-butyl, and tert-butyl) reference to one member of the group (e.g., n-butyl) is intended to include the remaining isomers (e.g., iso-butyl, sec-butyl, and tert-butyl) in the family, unless otherwise specified herein. Likewise, reference to an alkyl, alkenyl, alkoxy, or aryl group without specifying a particular isomer (e.g., butyl) includes all isomers (e.g., n-butyl, iso-butyl, sec-butyl, and tert-butyl).

For any particular compound disclosed herein, any general or specific structure presented also encompasses all conformational isomers, regioisomers, and stereoisomers that may arise from a particular set of substituents, unless stated otherwise. Similarly, unless stated otherwise, the general or specific structure also encompasses all enantiomers, diastereomers, and other optical isomers whether in enantiomeric or racemic forms, as well as mixtures of stereoisomers, as would be recognized by a skilled artisan. In some embodiments, the compounds described herein can contain one or more chiral centers. Disclosure of such compounds, unless otherwise specified, includes racemic mixtures, diastereomers, enantiomers, and mixtures containing one or more stereoisomer. Further, unless otherwise specified, the disclosed compounds encompass racemic forms of the compounds in addition to individual stereoisomers, as well as mixtures containing any of these. The word "compound," as used herein, includes any chemical structure in which two or more chemical elements are bonded together. Thus, "compound" includes, but is not limited to, small molecules, cross-linkers, monofunctional molecules, monomers, and polymers.

The term "ring atom" refers to an atom that is part of a cyclic ring structure. By this definition, a benzyl group has six ring atoms and tetrahydrofuran has five ring atoms. A heterocyclic ring is a ring having a heteroatom in the ring structure (i.e., one of the ring atoms is a heteroatom) as opposed to a heteroatom-substituted ring where a ring atom is bonded to a heteroatom that is not a ring atom. For example, tetrahydrofuran is a heterocyclic ring and 4-N,N-dimethylamino-phenyl is a heteroatom-substituted ring.

FIG. 1A shows various classes of azole corrosion inhibitors that can be used for embodiments of ultraviolet-stabilized corrosion inhibitors described herein. The classes include benzotriazoles 100, benzothiazoles 102, benzoxazoles 104, 1,2,4-triazoles 106, tetrazoles 108, 1,3,4-thiadiazoles 110, pyrazoles 112, and imidazoles 114. More than one R group may be present on the azole corrosion inhibitor. If there is more than one R group on the azole corrosion inhibitor, the R groups can be the same or different.

In embodiments described herein, the azole is chemically modified with a photosensitizer material. The photosensitizer material, such as oxybenzone 120 (shown in FIG. 1B), functions by absorbing UVA/B light and converting it to vibrational energy. Other photosensitizers include avobenzone, octisalate, octocrylene, homosalate, octinoxate, and derivatives thereof.

Figure 1B:
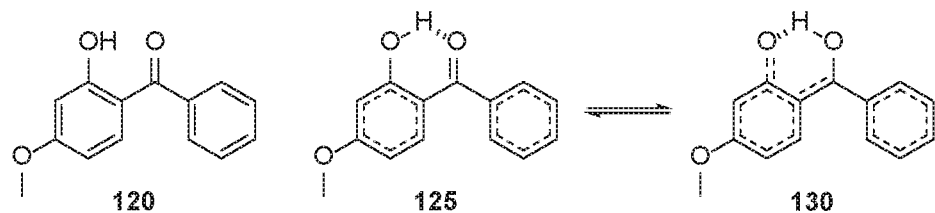
FIG. 1B is a chemical reaction diagram of an excited state enol to keto tautomerization for oxybenzone absorbing UVA/B light.
Figure 1C:
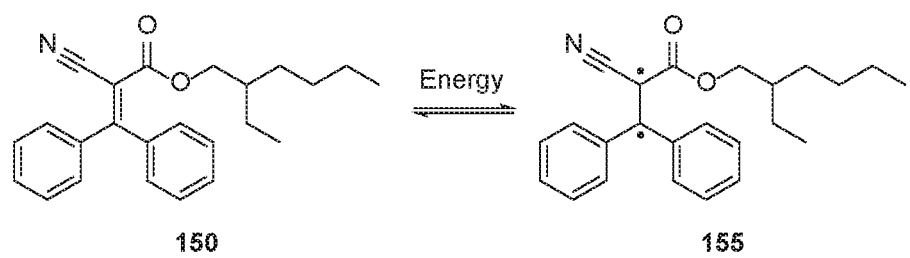
FIG. 1C is a chemical reaction diagram of a photochemical reaction of octocrylene useful for embodiments described herein.

In some embodiments, the photoprotective properties can be understood in terms of an initial ultrafast excited state enol 125 to keto 130 tautomerization, as shown in FIG. 1B. This is followed by efficient internal conversion, and subsequent vibrational relaxation to the ground state (enol) tautomer. The same principles apply to octisalate, octocrylene, octinoxate, and homosalate photosensitizer molecules that are described herein. For example, the photochemical reaction of octocrylene 150 to an excited state octocrylene 155 upon absorption of energy is depicted in FIG. 1C.

Given these characteristics, photosensitizers can be used to protect molecules from UV light degradation as the photosensitizers will take up the energy provided by the UV light. This process can happen entirely within the photosensitizer block, or it can happen through a conjugated azole-photosensitizer system, wherein the direct bonding of azole to the photosensitizer results in overlapping wavefunctions of the pi-electron orbitals. This allows for any UV light-induced excitation that occurs on the azole to be delocalized over the azole-photosensitizer system, and will prevent the azole from undergoing photodegradation. Additionally, the close proximity of the azole moiety with the photosensitizer moiety will likely cause other excited state transfer processes to occur, e.g., intersystem crossing and Fourier Resonance Energy Transfer (FRET). FRET is most efficient at approximately 1 to 10 nm, so having the photosensitizer near the azole is critical. Intersystem crossing that may occur across atoms/orbitals operates under a similar proximity system. These excited states have certain lifetimes and the further that these excited states have to travel to reach a desired point in the molecule (e.g., a photosensitizer moiety), the less likely they are to make it there without succumbing to another decay process.

As described below, a variety of azoles and photosensitizers can be synthesized. Cross-coupling (e.g., Suzuki and Sonogashira) of the azole and photosensitizer then provides the ultraviolet-stabilized corrosion inhibitor.

Example Photosensitizers

It is contemplated that any photosensitizer that can be cross-coupled to an azole can be used to form the ultraviolet-stabilized corrosion inhibitor. Such photosensitizers and precursors to photosensitizers include: avobenzone, oxybenzone, octisalate, octocrylene, homosalate, octinoxate, and derivatives thereof; 4-bromo-2-hydroxybenzoic acid; 2-bromo-6-hydroxybenzoic acid; 5-Bromosalicylic acid; 2-bromo-4,6-dimethyl-3-hydroxybenzoic acid; 3-hydroxybenzoic acid; 4-bromobenzophenone; 3-bromobenzophenone; 2-bromobenzophenone; 2-amino-4'-bromobenzophenone; 2-acetoxy-2'-bromobenzophenone; 3-azetidinomethyl-3'-bromobenzophenone; 4-acetoxy-2'-bromobenzophenone; 4-acetoxy-3'-bromobenzophenone; 4-bromobenzophenone ethylene ketal; 4'-azetidinomethyl-3-bromobenzophenone; 2-acetoxy-3'-bromobenzophenone; 2-acetoxy-4'-bromobenzophenone; 3-acetoxy-2'-bromobenzophenone; 3-acetoxy-3'-bromobenzophenone; 3-acetoxy-4'-bromobenzophenone; 3-azetidinomethyl-4'-bromobenzophenone; 4-acetoxy-4'-bromobenzophenone; 4-azetidinomethyl-4'-bromobenzophenone; 3,5-dibromobenzaldehyde; 2,5-dibromobenzaldehyde; 2,4-dibromobenzaldehyde; 2-amino-3,5-dibromobenzaldehyde; and 3,5-dibromosalicylaldehyde. Such photosensitizers are commercially available from Sigma-Aldrich.

Figure 2A:
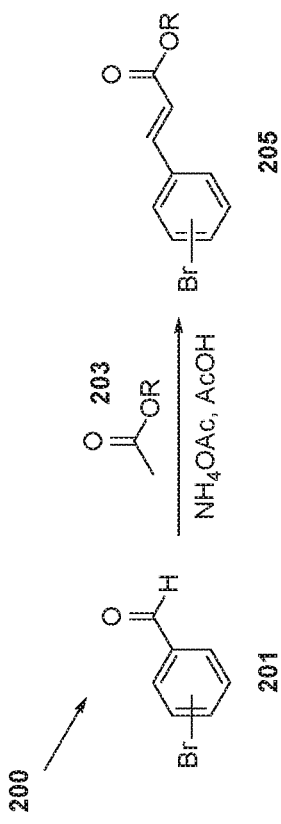
FIG. 2A is a chemical reaction diagram of a method 200 of forming a photosensitizer according to some embodiments.

FIG. 2A illustrates a method 200 of forming an octinoxate type photosensitizer 205 according to some embodiments. In method 200, the octinoxate type photosensitizer 205 is formed from an aldehyde 201 and an acetate ester 203 via an aldol condensation reaction. Aldehyde 201 is an aldehyde attached to an aromatic ring, and the aromatic ring has a bromine atom also attached to it (e.g., 4-bromobenzaldehyde). The aldehyde 201 may additionally comprise other functionality in addition to the bromine atom such as halogen, alkoxy, heteroatom (e.g., —OH, —NH$_2$), alkyl (substituted or unsubstituted), aryl (substituted or unsubstituted), and heteroaryl (substituted or unsubstituted).

Octinoxate type photosensitizer 205 can be synthesized according to the following prophetic procedure. To a solution of aldehyde 201 in acetic acid (AcOH) is added ammonium acetate (NH$_4$OAc, excess) and alkyl ester 203. The reaction mixture is heated to a temperature of about 100° C. or reflux for about 2 hours and monitored for completion by thin layer chromatography. The reaction mixture is then cooled to room temperature and diluted with water. The reaction mixture is extracted three times with hexane or a solvent mixture that is 3:1 hexane/ethyl acetate. The combined organic fractions are rinsed with sodium bicarbonate and brine, and dried over sodium sulfate. The solvents are removed in vacuo and the crude residue is purified by fractional distillation or column chromatography to produce the octinoxate type photosensitizer 205 as a bromide. R can be an alkyl radical (such as a $C_1$ to $C_{20}$ alkyl radical, for example a $C_1$ to $C_8$ alkyl radical), a substituted alkyl radical (such as a $C_1$ to $C_{20}$ substituted alkyl radical, for example a $C_1$ to $C_8$ substituted alkyl radical), an alkenyl radical (such as a $C_1$ to $C_{20}$ alkenyl radical, for example a $C_1$ to $C_8$ alkenyl radical), a substituted alkenyl radical (such as a $C_1$ to $C_{20}$ substituted alkyl radical, for example a $C_1$ to $C_8$ substituted alkenyl radical), an alkoxy radical (such as a $C_1$ to $C_{20}$ alkoxy radical, such as an ethylene glycol and a polyethylene glycol), or a substituted alkoxy radical (such as a $C_1$ to $C_{20}$ substituted alkoxy radical, for example a $C_1$ to $C_8$ substituted alkoxy radical). R may also include an aryl group (such as an unsubstituted $C_4$ to $C_{20}$ aryl ring, such as an unsubstituted $C_6$ to $C_{14}$ aryl ring, and a substituted $C_4$ to $C_{20}$ aryl ring, such as a substituted $C_6$ to $C_{14}$ aryl ring) and a heteroaryl group (such as an unsubstituted $C_4$ to $C_{20}$ heteroaryl ring, such as an unsubstituted $C_6$ to $C_{14}$ heteroaryl ring, and a substituted $C_4$ to $C_{20}$ heteroaryl ring, such as a substituted $C_6$ to $C_{14}$ heteroaryl ring).

It should be noted that the bromine substituent may be at any position along the phenyl ring relative to the carbonyl substituent (e.g., ortho, meta, or para). Thus, and in some embodiments, for the bromide materials herein (e.g., bromide 201, bromide 301, bromide 401, bromide 455, and bromide 501), the position of the bromine can be varied relative to another substituent on the aromatic ring (e.g., the hydrocarbyl radical or substituted hydrocarbyl radical, for example the carbonyl). Such bromides can be purchased commercially or can be synthesized via standard Friedel-Crafts chemistry. For example, 2-bromobenzaldehyde (e.g., 201, where the bromine is ortho to the aldehyde) is commercially available from Sigma-Aldrich. Alternatively, and for example, (3-bromo-phenyl)-(2-hydroxy-4-methoxyphenyl)-methanone (i.e., 501a in FIG. 5) is an oxybenzone having the bromide meta to the carbonyl substituent, and can be made from a Friedel-Crafts reaction of 3-bromobenzoyl chloride with 3-methoxyphenol. Because the bromide can be ortho, meta, or para to another group (e.g., the carbonyl group), the alkyne group can be ortho, meta, or para to another group (e.g., the carbonyl group).

Figure 2B:
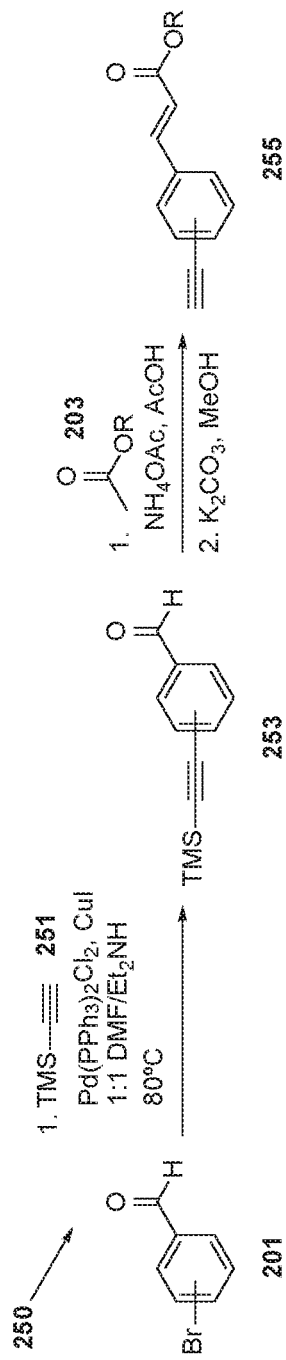
FIG. 2B is a chemical reaction diagram of a method 250 of forming a photosensitizer according to some embodiments.

FIG. 2B illustrates a method 250 of forming an octinoxate type photosensitizer 255 according to some embodiments. In method 250, the aldehyde 201 reacts with a trimethylsilylacetylene 251 via a Sonogashira cross-coupling reaction to form an alkyne 253. The alkyne can then be reacted with the acetate ester 203 via an aldol condensation to form a vinylogous ester (not shown). A subsequent deprotection is used to remove the trimethylsilyl group and form the octinoxate type photosensitizer 255 as an alkyne. In some embodiments, the aldol condensation is performed before the Sonogashira cross-coupling. Of note, trimethylsilylacetylene 251 may have a different silyl group, such as triethylsilyl, tert-butyldimethylsilyl, and triisopropylsilyl, instead of the trimethylsilyl group. The variety of silyl groups allow for varying substrate tolerance when varying reaction conditions.

The octinoxate type photosensitizer 255 can be synthesized according to the following prophetic procedure. To a stirred deoxygenated solution of aldehyde 201 and trimethylsilylacetylene 251 in an organic solvent which is an alkylamine (e.g., trimethylamine (Et$_3$N), or diethylamine (Et$_2$NH)) or a mixture of alkylamine and an organic solvent such as N,N-dimethylformamide (DMF), dichloromethane (DCM), or tetrahydrofuran (THF) at about 25° C., is added a palladium catalyst (e.g., bis(triphenylphosphine)palladium (II) dichloride (Pd(PPh$_3$)$_2$Cl$_2$)) and a copper catalyst (e.g., copper(I) iodide (CuI)). The reaction mixture is heated and maintained at a temperature of about 80° C. Upon completion of the reaction which is monitored by thin layer chromatography, the solvent is removed in vacuo, and the resulting slurry is subjected to either standard aqueous workup conditions or filtration conditions. The crude product is purified by recrystallization, column chromatography, or by other techniques known in the art. Formation of the vinylogous ester (not shown) by reaction with alkyl ester 203 may be accomplished by the procedure provided above. The vinylogous ester is then transformed to the octinoxate type photosensitizer 255 as an alkyne according to the following prophetic procedure. To a stirring solution of vinylogous ester (1 equiv.) in a solvent or solvent mixture (e.g., 1:1 DCM/methanol (MeOH)) is added 1.1 equiv. of mild base (e.g., potassium carbonate (K$_2$CO$_3$)). The reaction mixture is stirred until completion, as monitored by thin layer chromatography, at which point, most of the solvent is removed in vacuo. The resulting slurry is added to water and extracted with DCM three times. The combined organic layers are washed with brine, dried over magnesium sulfate (MgSO$_4$), filtered, and the solvents removed in vacuo. The crude product is purified via column chromatography or by standard procedures to produce the octinoxate type photosensitizer 255 as an alkyne. R can be an alkyl radical (such as a $C_1$ to $C_{20}$ alkyl radical, for example a $C_1$ to $C_8$ alkyl radical), a substituted alkyl radical (such as a $C_1$ to $C_{20}$ substituted alkyl radical, for example a $C_1$ to $C_8$ substituted alkyl radical), an alkenyl radical (such as a $C_1$ to $C_{20}$ alkenyl radical, for example a $C_1$ to $C_8$ alkenyl radical), a substituted alkenyl radical (such as a $C_1$ to $C_{20}$ substituted alkyl radical, for example a $C_1$ to $C_8$ substituted alkenyl radical), an alkoxy radical (such as a $C_1$ to $C_{20}$ alkoxy radical, such as an ethylene glycol and a polyethylene glycol), or a substituted alkoxy radical (such as a $C_1$ to $C_{20}$ substituted alkoxy radical, for example a $C_1$ to $C_8$ substituted alkoxy radical). R may also include an aryl group (such as an unsubstituted $C_4$ to $C_{20}$ aryl ring, such as an unsubstituted $C_6$ to $C_{14}$ aryl ring, and a substituted $C_4$ to $C_{20}$ aryl ring, such as a substituted $C_6$ to $C_{14}$ aryl ring) and a heteroaryl group (such as an unsubstituted $C_4$ to $C_{20}$ heteroaryl ring, such as an unsubstituted $C_6$ to $C_{14}$ heteroaryl ring, and a substituted $C_4$ to $C_{20}$ heteroaryl ring, such as a substituted $C_6$ to $C_{14}$ heteroaryl ring).

FIG. 3A illustrates a method 300 of forming an octocrylene type photosensitizer 305 according to some embodiments. In method 300, the octocrylene type photosensitizer 305 is formed from a bromine functionalized benzophenone 301 and an alkyl-2-cyanoate 303 via an aldol condensation reaction. The bromine functionalized benzophenone 301

(e.g., 4-bromobenzophenone). The bromine functionalized benzophenone 301 may additionally comprise other functionality in addition to the bromine atom such as halogen, alkoxy, heteroatom (e.g., —OH, —NH$_2$), alkyl (substituted or unsubstituted), aryl (substituted or unsubstituted), and heteroaryl (substituted or unsubstituted).

The octocrylene type photosensitizer 305 can be synthesized according to the following prophetic procedure. To a reaction vessel is added an alkyl cyanoacetate 303 (0.32 mol), a bromine-functionalized benzophenone 301 (0.45 mol), ammonium acetate (0.36 mol), propionic acid (1.1 mol), and heptane (81.0 g). The mixture is heated under stirring. When the temperature reaches about 110° C., a mixture of propionic acid, water, and heptane is distilled off from the vessel over a period of about 5 hours at normal pressure. The heptane phase is returned back to the vessel. The reactant is then cooled to about 90° C., and 100 mL of hot water is added to the reaction mixture. The mixture is kept at about 85° C. for about 10 minutes, and then transferred to a funnel for separation. Standard procedures for separation, solvent removal, and purification are then performed to produce the octocrylene type photosensitizer 305 as a bromide. R can be an alkyl radical (such as a $C_1$ to $C_{20}$ alkyl radical, for example a $C_1$ to $C_8$ alkyl radical), a substituted alkyl radical (such as a $C_1$ to $C_{20}$ substituted alkyl radical, for example a $C_1$ to $C_8$ substituted alkyl radical), an alkenyl radical (such as a $C_1$ to $C_{20}$ alkenyl radical, for example a $C_1$ to $C_8$ alkenyl radical), a substituted alkenyl radical (such as a $C_1$ to $C_{20}$ substituted alkyl radical, for example a $C_1$ to $C_8$ substituted alkenyl radical), an alkoxy radical (such as a $C_1$ to $C_{20}$ alkoxy radical, such as an ethylene glycol and a polyethylene glycol), or a substituted alkoxy radical (such as a $C_1$ to $C_{20}$ substituted alkoxy radical, for example a $C_1$ to $C_8$ substituted alkoxy radical). R may also include an aryl group (such as an unsubstituted $C_4$ to $C_{20}$ aryl ring, such as an unsubstituted $C_6$ to $C_{14}$ aryl ring, and a substituted $C_4$ to $C_{20}$ aryl ring, such as a substituted $C_6$ to $C_{14}$ aryl ring) and a heteroaryl group (such as an unsubstituted $C_4$ to $C_{20}$ heteroaryl ring, such as an unsubstituted $C_6$ to $C_{14}$ heteroaryl ring, and a substituted $C_4$ to $C_{20}$ heteroaryl ring, such as a substituted $C_6$ to $C_{14}$ heteroaryl ring). The phenyl ring in 301 may additionally comprise a methoxy substituent. In such cases, the synthesis is similar to that described above, starting with the bromophenyl, methoxyphenyl aldehyde (methanone).

FIG. 3B illustrates a method 350 of forming an octocrylene type photosensitizer 355 according to some embodiments. In method 350, the aldehyde 301 reacts with a trimethylsilylacetylene 251 via a Sonogashira cross-coupling reaction to form an alkyne 353. The alkyne 353 can then be reacted with an alkyl-2-cyanoate 303 via an aldol condensation to form a vinylogous ester (not shown). A subsequent deprotection is used to remove the trimethylsilyl group and form the octocrylene type photosensitizer 355 as an alkyne. In some embodiments, the aldol condensation is performed before the Sonogashira cross-coupling. Of note, trimethylsilylacetylene 251 may have a different silyl group, such as triethylsilyl, tert-butyldimethylsilyl, and triisopropylsilyl, instead of the trimethylsilyl group. The variety of silyl groups allow for varying substrate tolerance when varying reaction conditions.

The octocrylene type photosensitizer 355 can be synthesized according to the following prophetic procedure. To a stirring deoxygenated solution of bromine-functionalized benzophenone 301 and trimethylsilylacetylene 251 in an organic solvent which is an alkylamine (e.g., Et$_3$N or Et$_2$NH) or a mixture of alkylamine and an organic solvent such as DMF, DCM, or THF at about 25° C., is added a palladium catalyst (e.g., Pd(PPh$_3$)$_2$Cl$_2$) and a copper catalyst (e.g., CuI). The reaction mixture is heated and maintained at a temperature of about 80° C. Upon completion of the reaction which is monitored by thin layer chromatography, the solvent is removed in vacuo, and the resulting slurry is subjected to by either standard aqueous workup conditions or filtration conditions. The crude product is purified by recrystallization, column chromatography, or by other techniques known in the art. Formation of the vinylogous ester (not shown) by reaction with an alkyl cyanoacetate 303 may be accomplished by the procedure provided above. The vinylogous ester is then transformed to the octocrylene type photosensitizer 355 as an alkyne according to the following prophetic procedure. To a stirring solution of vinylogous ester (1 equiv.) in a solvent or solvent mixture (e.g., 1:1 DCM/methanol (MeOH)) is added 1.1 equiv. of mild base (e.g., potassium carbonate (K$_2$CO$_3$)). The reaction mixture is stirred until completion, as monitored by thin layer chromatography, at which point, most of the solvent is removed in vacuo. The resulting slurry is added to water and extracted with DCM three times. The combined organic layers are washed with brine, dried over magnesium sulfate (MgSO$_4$), filtered, and the solvents removed in vacuo. The crude product is purified via column chromatography or by standard procedures to produce the octocrylene type photosensitizer 355 as an alkyne. R can be an alkyl radical (such as a $C_1$ to $C_{20}$ alkyl radical, for example a $C_1$ to $C_8$ alkyl radical), a substituted alkyl radical (such as a $C_1$ to $C_{20}$ substituted alkyl radical, for example a $C_1$ to $C_8$ substituted alkyl radical), an alkenyl radical (such as a $C_1$ to $C_{20}$ alkenyl radical, for example a $C_1$ to $C_8$ alkenyl radical), a substituted alkenyl radical (such as a $C_1$ to $C_{20}$ substituted alkyl radical, for example a $C_1$ to $C_8$ substituted alkenyl radical), an alkoxy radical (such as a $C_1$ to $C_{20}$ alkoxy radical, such as an ethylene glycol and a polyethylene glycol), or a substituted alkoxy radical (such as a $C_1$ to $C_{20}$ substituted alkoxy radical, for example a $C_1$ to $C_8$ substituted alkoxy radical). R may also include an aryl group (such as an unsubstituted $C_4$ to $C_{20}$ aryl ring, such as an unsubstituted $C_6$ to $C_{14}$ aryl ring, and a substituted $C_4$ to $C_{20}$ aryl ring, such as a substituted $C_6$ to $C_{14}$ aryl ring) and a heteroaryl group (such as an unsubstituted $C_4$ to $C_{20}$ heteroaryl ring, such as an unsubstituted $C_6$ to $C_{14}$ heteroaryl ring, and a substituted $C_4$ to $C_{20}$ heteroaryl ring, such as a substituted $C_6$ to $C_{14}$ heteroaryl ring).

Figure 4A:
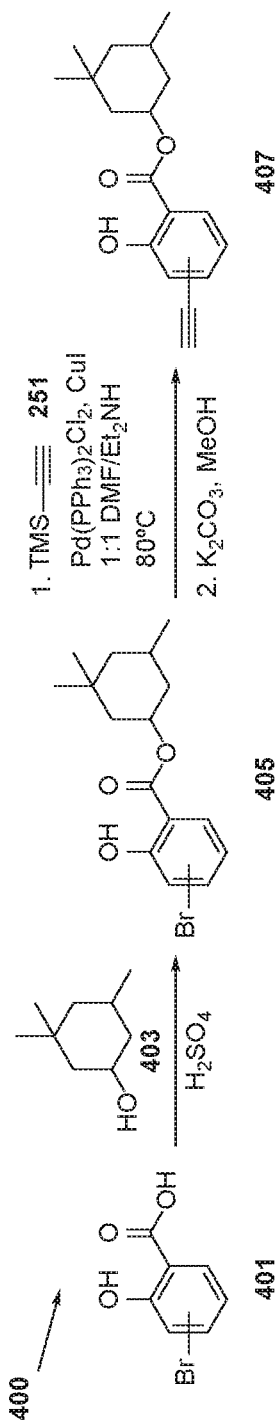
FIG. 4A is a chemical reaction diagram of a method 400 of forming a photosensitizer according to some embodiments.

FIG. 4A illustrates a method 400 of forming a homosalate type photosensitizer 407 according to some embodiments. In method 400, a bromine functionalized carboxylic acid 401 (with or without the hydroxyl, e.g., 4-bromo-2-hydroxybenzoic acid and 4-bromobenzoic acid) reacts with a 3,3,5-trimethylcyclohexanol 403 via a Fisher esterification to form an ester 405. The bromine functionalized carboxylic acid 401 (e.g., 4-bromo-2-hydroxybenzoic acid) may additionally comprise other functionality in addition to the bromine atom such as halogen, alkoxy, heteroatom (e.g., —OH, —NH$_2$), alkyl (substituted or unsubstituted), aryl (substituted or unsubstituted), and heteroaryl (substituted or unsubstituted).

A Sonogashira cross-coupling reaction of the ester 405 with a trimethylsilylacetylene 251 and a subsequent deprotection to remove the trimethylsilyl group forms the homosalate type photosensitizer 407 as an alkyne. Of note, trimethylsilylacetylene 251 may have a different silyl group, such as triethylsilyl, tert-butyldimethylsilyl, and triisopropylsilyl, instead of the trimethylsilyl group. The variety of silyl groups allow for varying substrate tolerance when varying reaction conditions.

The homosalate type photosensitizer 407 can be synthesized according to the following prophetic procedure. A solution of carboxylic acid 401 (1.0 equiv.), 3,3,5,5-trimethylcyclohexanol 403 (1.05 equiv.), and concentrated sulfuric acid ($H_2SO_4$, 1.8-2.0 equiv.) is refluxed for about 8 hours, monitoring for completion of the reaction by thin layer chromatography. The reaction mixture is poured into cold water and extracted with diethyl ether three times. The combined organic phases are washed with water (two times), sodium bicarbonate (two times), and brine (one time), and dried over magnesium sulfate. The solvent is removed in vacuo, and the crude residue is purified by standard procedures for purification (such as fractional distillation) to provide ester 405. To a stirring deoxygenated solution of ester 405 and trimethylsilylacetylene 251 in an organic solvent which is an alkylamine (e.g., $Et_3N$ or $Et_2NH$) or a mixture of alkylamine and an organic solvent such as DMF, DCM, or THF at about 25° C., is added a palladium catalyst (e.g., $Pd(PPh_3)_2Cl_2$) and a copper catalyst (e.g., CuI). The reaction mixture is heated and maintained at a temperature of about 80° C. Upon completion of the reaction which is monitored by thin layer chromatography, the solvent is removed in vacuo, and the resulting slurry is subjected to either standard aqueous workup conditions or filtration conditions. The crude product is purified by recrystallization, column chromatography, or by techniques known in the art to produce a silylalkyne (not shown). The silylalkyne is then transformed to the homosalate type photosensitizer 407 as an alkyne according to the following prophetic procedure. To a stirring solution of the silylalkyne (1 equiv.) in a solvent or solvent mixture (e.g., 1:1 DCM/methanol (MeOH)) is added 1.1 equiv. of mild base (e.g., potassium carbonate ($K_2CO_3$)). The reaction mixture is stirred until completion, as monitored by thin layer chromatography, at which point, most of the solvent is removed in vacuo. The resulting slurry is added to water and extracted with DCM three times. The combined organic layers are washed with brine, dried over magnesium sulfate ($MgSO_4$), filtered, and the solvents removed in vacuo. The crude product is purified via column chromatography or by standard procedures to produce the homosalate type photosensitizer 407 as an alkyne. R can be an alkyl radical (such as a $C_1$ to $C_{20}$ alkyl radical, for example a $C_1$ to $C_8$ alkyl radical), a substituted alkyl radical (such as a $C_1$ to $C_{20}$ substituted alkyl radical, for example a $C_1$ to $C_8$ substituted alkyl radical), an alkenyl radical (such as a $C_1$ to $C_{20}$ alkenyl radical, for example a $C_1$ to $C_8$ alkenyl radical), a substituted alkenyl radical (such as a $C_1$ to $C_{20}$ substituted alkyl radical, for example a $C_1$ to $C_8$ substituted alkenyl radical), an alkoxy radical (such as a $C_1$ to $C_{20}$ alkoxy radical, such as an ethylene glycol and a polyethylene glycol), or a substituted alkoxy radical (such as a $C_1$ to $C_{20}$ substituted alkoxy radical, for example a $C_1$ to $C_8$ substituted alkoxy radical). R may also include an aryl group (such as an unsubstituted $C_4$ to $C_{20}$ aryl ring, such as an unsubstituted $C_6$ to $C_{14}$ aryl ring, and a substituted $C_4$ to $C_{20}$ aryl ring, such as a substituted $C_6$ to $C_{14}$ aryl ring) and a heteroaryl group (such as an unsubstituted $C_4$ to $C_{20}$ heteroaryl ring, such as an unsubstituted $C_6$ to $C_{14}$ heteroaryl ring, and a substituted $C_4$ to $C_{20}$ heteroaryl ring, such as a substituted $C_6$ to $C_{14}$ heteroaryl ring).

Figure 4B:
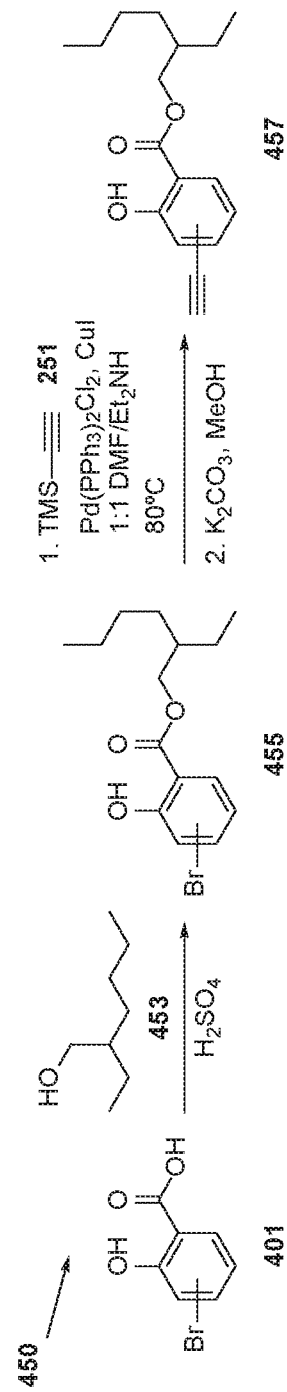
FIG. 4B is a chemical reaction diagram of a method 450 of forming a photosensitizer according to some embodiments.

FIG. 4B illustrates a method 450 of forming an octisalate type photosensitizer 457 according to some embodiments. In method 450, a carboxylic acid 401 reacts with a 2-ethylhexanol 453 via a Fisher esterification to form an ester 455. A Sonogashira cross-coupling reaction of the ester 455 with a trimethylsilylacetylene 251 and a subsequent deprotection to remove the trimethylsilyl group then forms the octisalate type photosensitizer 457 as an alkyne. Of note, trimethylsilylacetylene 251 may have a different silyl group, such as triethylsilyl, tert-butyldimethylsilyl, and triisopropylsilyl, instead of the trimethylsilyl group. The variety of silyl groups allow for varying substrate tolerance when varying reaction conditions.

The octisalate type photosensitizer 457 can be synthesized according to the following prophetic procedure. A solution of carboxylic acid 401 (1.0 equiv.), 2-ethylcyclohexanol 453 (1.05 equiv.), and concentrated sulfuric acid ($H_2SO_4$, 1.8-2.0 equiv.) is refluxed for about 8 hours, monitoring for completion of the reaction by thin layer chromatography. The reaction mixture is poured into cold water and extracted with diethyl ether three times. The combined organic phases are washed with water (two times), sodium bicarbonate (two times), and brine (one time), and dried over magnesium sulfate. The solvent is removed in vacuo, and the crude residue is purified by standard procedures for purification (such as fractional distillation) to provide ester 455. To a stirring deoxygenated solution of ester 455 and trimethylsilylacetylene 251 in an organic solvent which is an alkylamine (e.g., $Et_3N$ or $Et_2NH$) or a mixture of alkylamine and an organic solvent such as DMF, DCM, or THF at about 25° C., is added a palladium catalyst (e.g., $Pd(PPh_3)_2Cl_2$) and a copper catalyst (e.g., CuI). The reaction mixture is heated and maintained at a temperature of about 80° C. Upon completion of the reaction which is monitored by thin layer chromatography, the solvent is removed in vacuo, and the resulting slurry is subjected to either standard aqueous workup conditions or filtration conditions. The crude product is purified by recrystallization, column chromatography, or by techniques known in the art to produce a silylalkyne (not shown). The silylalkyne is then transformed to the octisalate type photosensitizer 457 according to the following prophetic procedure. To a stirring solution of silylalkyne (1 equiv.) in a solvent or solvent mixture (e.g., 1:1 DCM/methanol (MeOH)) is added 1.1 equiv. of mild base (e.g., potassium carbonate ($K_2CO_3$)). The reaction mixture is stirred until completion, as monitored by thin layer chromatography, at which point, most of the solvent is removed in vacuo. The resulting slurry is added to water and extracted with DCM three times. The combined organic layers are washed with brine, dried over magnesium sulfate ($MgSO_4$), filtered, and the solvents removed in vacuo. The crude product is purified via column chromatography or by standard procedures to produce the octisalate type photosensitizer 457 as an alkyne. R can be an alkyl radical (such as a $C_1$ to $C_{20}$ alkyl radical, for example a $C_1$ to $C_8$ alkyl radical), a substituted alkyl radical (such as a $C_1$ to $C_{20}$ substituted alkyl radical, for example a $C_1$ to $C_8$ substituted alkyl radical), an alkenyl radical (such as a $C_1$ to $C_{20}$ alkenyl radical, for example a $C_1$ to $C_8$ alkenyl radical), a substituted alkenyl radical (such as a $C_1$ to $C_{20}$ substituted alkyl radical, for example a $C_1$ to $C_8$ substituted alkenyl radical), an alkoxy radical (such as a $C_1$ to $C_{20}$ alkoxy radical, such as an ethylene glycol and a polyethylene glycol), or a substituted alkoxy radical (such as a $C_1$ to $C_{20}$ substituted alkoxy radical, for example a $C_1$ to $C_8$ substituted alkoxy radical). R may also include an aryl group (such as an unsubstituted $C_4$ to $C_{20}$ aryl ring, such as an unsubstituted $C_6$ to $C_{14}$ aryl ring, and a substituted $C_4$ to $C_{20}$ aryl ring, such as a substituted $C_6$ to $C_{14}$ aryl ring) and a heteroaryl group (such as an unsubstituted $C_4$ to $C_{20}$ heteroaryl ring, such as an unsubstituted $C_6$ to $C_{14}$ heteroaryl ring, and a substituted $C_4$ to $C_{20}$ heteroaryl ring, such as a substituted $C_6$ to $C_{14}$ heteroaryl ring).

Figure 5:
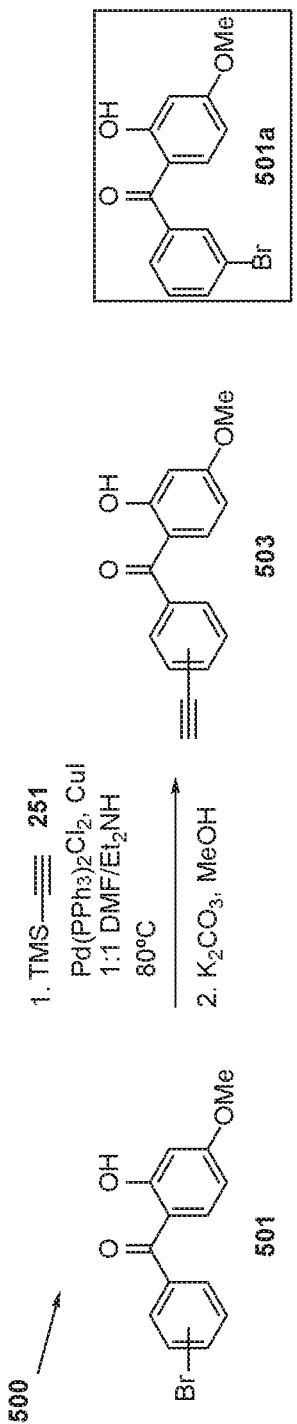
FIG. 5 is a chemical reaction diagram of a method 500 of forming a photosensitizer according to some embodiments.

FIG. 5 illustrates a method 500 of forming an oxybenzone type photosensitizer 503 according to some embodiments. In method 500, a bromide 501 ((4-bromophenyl)-(2-hydroxy-4-methoxyphenyl)-methanone) reacts with a trimethylsilylacetylene 251 in a Sonogashira cross-coupling reaction. A subsequent deprotection to remove the trimethylsilyl group forms the oxybenzone type photosensitizer 503 as an alkyne. Of note, trimethylsilylacetylene 251 may have a different silyl group, such as triethylsilyl, tert-butyldimethylsilyl, and triisopropylsilyl, instead of the trimethylsilyl group. The variety of silyl groups allow for varying substrate tolerance when varying reaction conditions. Bromide 501 may additionally comprise other functionality in addition to the bromine atom such as halogen, alkoxy, heteroatom (e.g., —OH, —NH$_2$), alkyl (substituted or unsubstituted), aryl (substituted or unsubstituted), and heteroaryl (substituted or unsubstituted).

The oxybenzone type photosensitizer 503 can be synthesized according to the prophetic procedures for the Sonogashira reactions and deprotection reactions provided above. Standard procedures for quenching, solvent removal, and purification after those reactions are performed to produce the oxybenzone type photosensitizer 503 as an alkyne.

As discussed earlier, the bromine substituent may be at any position along the phenyl ring relative to the carbonyl substituent (e.g., ortho, meta, or para). Thus, and in some embodiments, for the bromide materials herein (e.g., bromide 201, bromide 301, bromide 401, bromide 455, and bromide 501), the position of the bromine relative to the other substituent (e.g., the carbonyl) can be varied. Such bromides can be purchased commercially or can be synthesized via standard Friedel-Crafts chemistry.

According to some embodiments, the bromide 501 is synthesized via a Friedel-Crafts reaction by the following prophetic procedure. To an oven-dried 5 mL microwave reaction tube charged with a mixture of 4-methoxyphenol (1 mmol) and anhydrous dichloromethane (1 mL) is added a solution of boron trichloride in dichloromethane (1 M solution, 1 mmol, 1 mL), followed by addition of a corresponding benzoyl chloride (1 mmol). The tube is capped and irradiated on a CEM Explorer. The mixture is stirred at about room temperature for about 1 hour to provide a two-phase solution. The organic layer is separated and the aqueous solution is extracted with ethyl acetate (3×5 mL). The combined organic phase is filtered through a short column packed with Celite® and anhydrous sodium sulfate. The filtrate is concentrated to about 2 mL, mixed with silica gel (about 1 g), and evaporated to dry. The mixture powder (which contains the product) is packed into an ISCO sample tube and purified on an ISCO Optix 10 parallel purification system using 4 g silica gel column, eluted with linear gradient hexane/ethyl acetate (0-30% in 10 min). The product is collected, evaporated using a Thermo-Savant Explorer HT evaporator, and dried under high vacuum to form bromide 501. This procedure may be used as a general Friedel-Crafts procedure to vary the position of the carbonyl relative to the bromide.

In some embodiments, bromide 301, bromide 401, bromide 405, bromide 455, and bromide 501 can also be used as the photosensitizer portion of the ultraviolet-stabilized azole.

The aforementioned bromides and alkynes can be cross-coupled with azoles via cross-coupling reactions to form the ultraviolet-stabilized azoles (i.e., the ultraviolet-stabilized corrosion inhibitors).

Example Azoles

As discussed above, various azoles (e.g., benzotriazole, benzothiazole, benzoxazoles, and derivatives thereof) can be used as corrosion inhibitors. Reaction of the azoles with a photosensitizer then forms the ultraviolet-stabilized corrosion inhibitors. It is contemplated that any azole that can be cross-coupled to a photosensitizer can be used to form the ultraviolet-stabilized corrosion inhibitor.

Figure 6A:
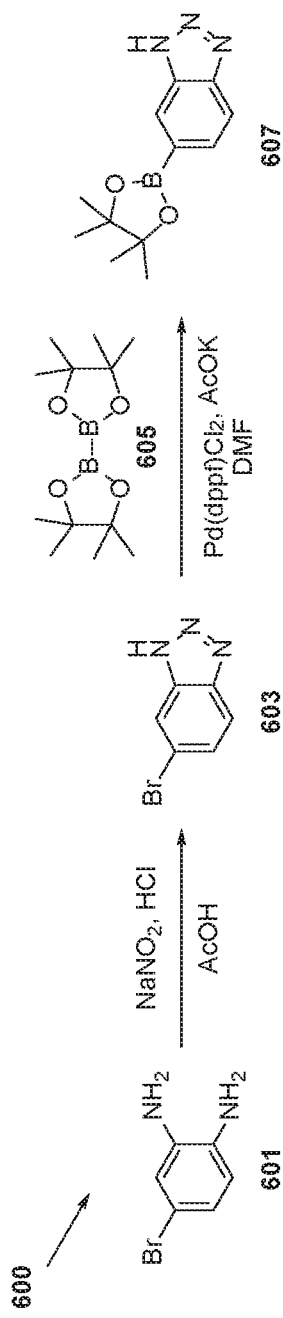
FIG. 6A is a chemical reaction diagram of a method 600 of forming a boronic ester benzotriazole according to some embodiments.

FIG. 6A illustrates a method 600 of forming a benzotriazole boronic ester 607 according to some embodiments. In method 600, 4-bromo-1,2-diaminobenzene 601 (commercially available from Sigma Aldrich, or can be synthesized by a reduction of 3-bromo-2-nitoraniline) is reacted with sodium nitrite (NaNO$_2$) under acidic conditions to form a 4-bromobenzotriazole 603. The 4-bromobenzotriazole 603 is then converted into the benzotriazole boronic ester 607 by a palladium catalyzed borylation with bis(pinacolato)diboron 605.

The benzotriazole boronic ester 607 may be synthesized according to the following prophetic procedure. To a solution of 4-bromo-1,2-diaminobenzene 601 (1.0 equiv.) and sodium nitrite (NaNO$_2$, 2.5 equiv.) in glacial acetic acid (AcOH) at 0° C. is added concentrated hydrochloric acid (HCl, 3-5 equiv.). The solution may also include water (1 part for every 3 parts of acetic acid). The reaction mixture is stirred for about 30 minutes and then diluted with water. The resulting mixture (which may include solids) is filtered, washed with water, and dried. The crude product is dissolved in hot ethanol and separated from residual solids via hot filtration. The solution is then cooled, filtered, and rinsed with cold ethanol and water to yield 4-bromobenzotriazole 603. 4-bromobenzotriazole 603 (1.0 equiv.), bis(pinacolato) diboron 605 (1.5 equiv.), and potassium acetate (AcOK, up to 6 equiv.) are dissolved in DMF. The solution is sparged with a nonreactive gas such as nitrogen or argon, and a catalyst such as [1,1'-bis(diphenylphosphino)ferrocene]dichloropalladium(II) (PdCl$_2$(dppf), 6 mol %)) is added. The reaction mixture is heated at about 85° C. under argon for about 48 hours, cooled to about room temperature, and diluted in 2.5 parts water. The mixture is then extracted with DCM or chloroform (three times). The combined organic layers are washed with water and brine, and dried over sodium sulfate. The solvents are removed in vacuo and the crude product is purified by column chromatography, recrystallization, or by other techniques known in the art to produce the benzotriazole boronic ester 607.

Figure 6B:
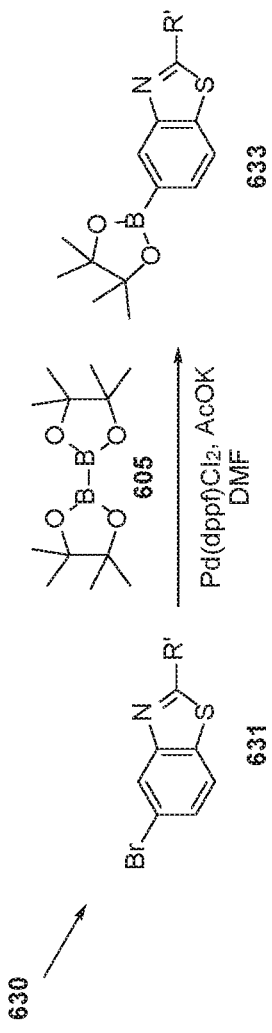
FIG. 6B is a chemical reaction diagram of a method 630 of forming a boronic ester benzothiazole according to some embodiments

FIG. 6B illustrates a method 630 of forming a boronic ester derivative of a benzothiazole boronic ester 633 according to some embodiments. In method 630, a bromine functionalized benzothiazole 631 is converted into the benzothiazole boronic ester 633 by a palladium catalyzed borylation with bis(pinacolato)diboron 605 according to the procedure above. Examples of bromine functionalized benzothiazoles include 5-bromobenzothiazole (R'=H), and bromine functionalized benzothiazoles where R' is a hydrocarbyl group, amino group, or thioether group such as 5-bromo-2-methyl-1,3-benzothiazole (R'=CH$_3$), 2-amino-5-bromobenzothiazole (R'=NH$_2$), and 5-bromo-2-(methylthio)benzo[d]thiazole (R'=S—CH$_3$). Such bromine functionalized benzothiazoles are commercially available from Sigma Aldrich. Additionally, the bromine functionalized benzothiazoles can include benzothiazoles where the bromine is in the 6-position, such as 6-bromo-1,3-benzothiazole (R'=H), and bromine functionalized benzothiazoles where R' is an hydrocarbyl group or an amino group such as 6-bromo-2-methylbenzothiazole (R'=$CH_3$) and 2-amino-6-bromobenzothiazole (R'=$NH_2$). Such bromine functionalized benzothiazoles where the bromine is in the 6-position are also commercially available from Sigma Aldrich. Moreover, the bromine functionalized benzothiazoles can include benzothiazoles where the bromine is in the 4-position, such as 4-bromo-1,3-benzothiazol-2-amine (R'=$NH_2$), which is commercially available from Sigma Aldrich.

Figure 6C:
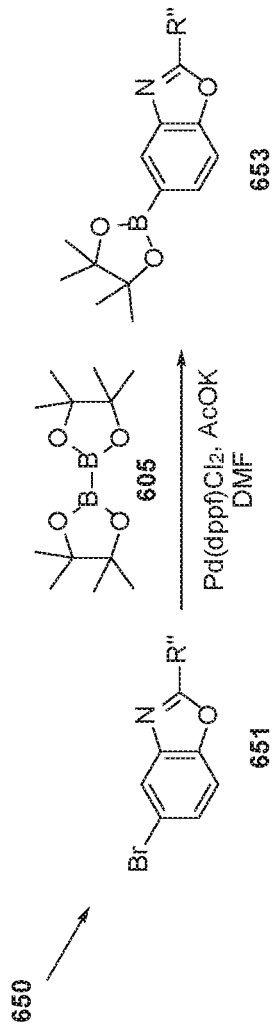
FIG. 6C is a chemical reaction diagram of a method 650 of forming a boronic ester benzoxazole according to some embodiments.

FIG. 6C illustrates a method 650 of forming a benzoxazole boronic ester 653 according to some embodiments. In method 650, a bromine functionalized benzoxazole 651 is converted into the benzoxazole boronic ester 653 by a palladium catalyzed borylation with bis(pinacolato)diboron 605 according to the procedure above. Examples of bromine functionalized benzoxazoles include 5-bromobenzooxazole (R"=H), bromine functionalized benzoxazoles where R" is a hydrocarbyl group such as 5-bromo-2-methylbenzoxazole (R"=$CH_3$), and bromine functionalized benzoxazoles where R" is an alkoxy group, an aryl group, or a heteroaryl group such as 5-bromo-2-(methoxymethyl)-1,3-benzoxazole (R"=$CH_2$—O—$CH_3$), 2-benzyl-5-bromo-1,3-benzoxazole (R"=benzyl), 5-bromo-2-phenyl-1,3-benzoxazole (R"=phenyl), and 5-bromo-2-(3-pyridinyl)-1,3-benzoxazole (R"=pyridinyl). Such bromine functionalized benzoxazoles are commercially available from Sigma Aldrich. Additionally, the bromine functionalized benzoxazoles can include benzoxazoles where the bromine is in the 6-position, such as 6-bromobenzoxazole (R"=H), and bromine functionalized benzoxazoles where R" is a hydrocarbyl group such as 6-bromo-2-methylbenzoxazole (R"=$CH_3$). Such bromine functionalized benzoxazoles where the bromine is in the 6-position are also commercially available from Sigma Aldrich. Moreover, the bromine functionalized benzoxazoles can include benzoxazoles where the bromine is in the 4-position or in the 7-position, such as 4-bromo-2-methyl-1,3-benzoxazole (R"=$CH_3$) and 7-bromo-2-methyl-1,3-benzoxazole (R"=$CH_3$) which is commercially available from Sigma Aldrich.

Example Cross-Couplings

The functionalized azoles can be covalently linked to the photosensitizers via a cross-coupling reaction (e.g., Suzuki cross-coupling and Sonogashira cross-coupling). The Suzuki cross-coupling can be used for any boronic ester and bromide cross-coupling reaction as described below. The Sonogashira cross-coupling can be used for any alkyne and bromide cross-coupling reaction as described below. The cross-coupling reactions result in the ultraviolet-stabilized corrosion inhibitors.

FIG. 7A illustrates a method 700 of forming an ultraviolet-stabilized corrosion inhibitor 703 as an ultraviolet-stabilized benzotriazole according to some embodiments. In FIG. 7A, G represents the rest of the photosensitizer (e.g., G is a hydrocarbyl or a substituted hydrocarbyl), and X can be hydrogen or a non-hydrogen (such as hydroxyl, amino, hydrocarbyl, thioether, and ether). As discussed above, the bromide can be ortho, meta, or para to the group represented by G, such as a carbonyl group. FIG. 7A shows the bromide group para to the group represented by G. In method 700, a Suzuki cross-coupling is used to cross-couple benzotriazole boronic ester 607 with a bromide represented by bromide 701 (e.g., bromide 205, bromide 305, bromide 405, bromide 455, and bromide 501) and form the ultraviolet-stabilized corrosion inhibitor 703.

The ultraviolet-stabilized corrosion inhibitor 703 may be synthesized according to the following prophetic procedure. Bromide 701 (1.0 equiv.), benzotriazole boronic ester 607 (1.2 equiv.) and tetrakis(triphenylphosphine)palladium(0) (Pd(PPh$_3$)$_4$, 5 mol %)) is dissolved in dry toluene (25 mL) under nitrogen. A deaerated $K_2CO_3$ solution (2M in 1:2 of water/ethanol) and a few drops of Aliquat 336 are added under nitrogen. The reaction mixture is refluxed for about 24 hours, and the reaction is monitored for completion by thin layer chromatography. The organic phase is filtered through a plug of Celite. Standard procedures for solvent removal and purification are then performed to produce the ultraviolet-stabilized corrosion inhibitor 703 as an ultraviolet-stabilized benzotriazole.

FIG. 7B illustrates a method 750 of forming an ultraviolet-stabilized corrosion inhibitor 753 as an ultraviolet-stabilized benzotriazole according to some embodiments. In FIG. 7B, G represents the rest of the photosensitizer (e.g., G is a hydrocarbyl or a substituted hydrocarbyl), and X can be hydrogen or a non-hydrogen (such as hydroxyl, amino, hydrocarbyl, thioether, and ether). As discussed above, the alkyne can be ortho, meta, or para to the group represented by G, such as a carbonyl group. FIG. 7B shows the alkyne group para to the group represented by G. In method 750, a Sonogashira cross-coupling is used to cross-couple 4-bromobenzotriazole 603 with an alkyne represented by alkyne 751 (e.g., alkyne 255, alkyne 355, alkyne 407, alkyne 457, and alkyne 503) and form the ultraviolet-stabilized corrosion inhibitor 753 as an ultraviolet-stabilized benzotriazole.

The ultraviolet-stabilized corrosion inhibitor 753 may be synthesized according to the following prophetic procedure. To a stirring deoxygenated solution of 4-bromobenzotriazole 603 and alkyne 751 in an organic solvent which is an alkylamine (e.g., Et$_3$N or Et$_2$NH) or a mixture of alkylamine and an organic solvent such as DMF, DCM, or THF at about 25° C., is added a palladium catalyst (e.g., Pd(PPh$_3$)$_2$Cl$_2$) and a copper catalyst (e.g., CuI). The reaction mixture is heated and maintained at a temperature of about 80° C. Upon completion of the reaction which is monitored by thin layer chromatography, the solvent is removed in vacuo, and the resulting slurry is subjected to either standard aqueous workup conditions or filtration conditions. The crude product is purified by recrystallization, column chromatography, or by techniques known in the art to form an ultraviolet-stabilized corrosion inhibitor 753 as an ultraviolet-stabilized benzotriazole.

Figure 8A:
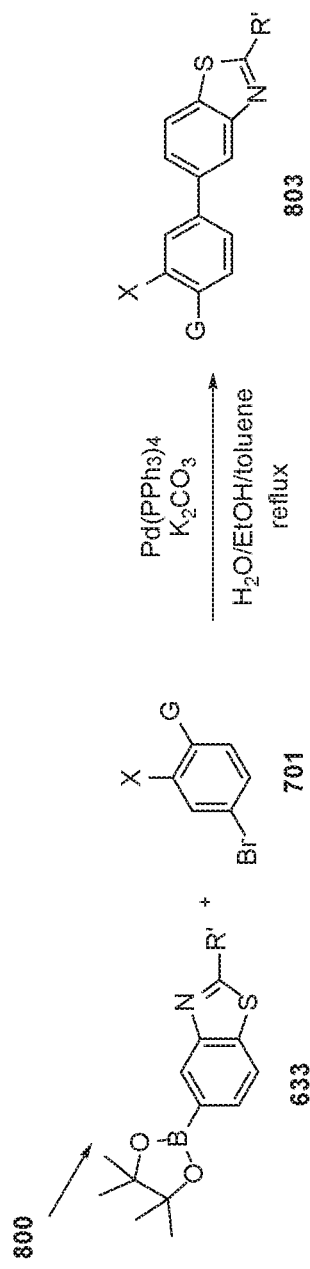
FIG. 8A is a chemical reaction diagram of a method 800 of forming an ultraviolet-stabilized corrosion inhibitor according to some embodiments.

FIG. 8A illustrates a method 800 of forming an ultraviolet-stabilized corrosion inhibitor 803 as an ultraviolet-stabilized benzothiazole according to some embodiments. In FIG. 8A, G represents the rest of the photosensitizer (e.g., G is a hydrocarbyl or a substituted hydrocarbyl), examples of R' of benzothiazole 633 are provided above, and X can be hydrogen or a non-hydrogen (such as hydroxyl, amino, hydrocarbyl, thioether, and ether). As discussed above, the bromide can be ortho, meta, or para to the group represented by G, such as a carbonyl group. FIG. 8A shows the bromide group para to the group represented by G. In method 800, a Suzuki cross-coupling is used to cross-couple a benzothiazole boronic ester 633 with a bromide represented by bromide 701 (e.g., bromide 205, bromide 305, bromide 405, bromide 455, bromide 501, and bromide 501a) and form the ultraviolet-stabilized corrosion inhibitor 803 as an ultraviolet-stabilized benzothiazole. The ultraviolet stabilized corrosion inhibitor 803 may be synthesized according to the prophetic Suzuki cross-coupling described above.

Figure 8B:
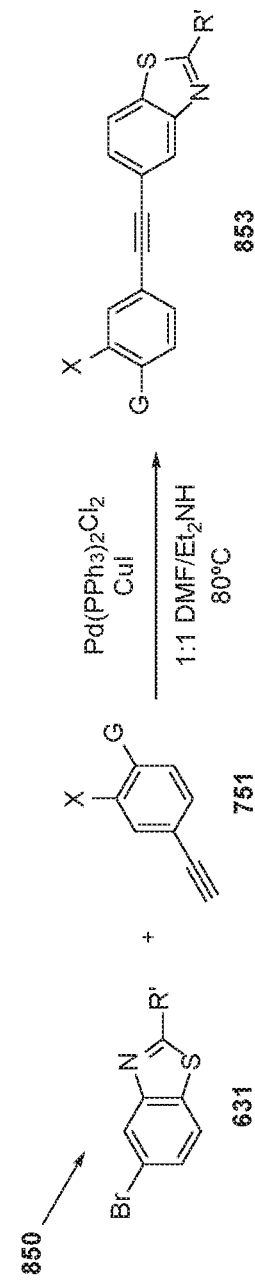
FIG. 8B is a chemical reaction diagram of a method 850 of forming an ultraviolet-stabilized corrosion inhibitor according to some embodiments.

FIG. 8B illustrates a method 850 of forming an ultraviolet-stabilized corrosion inhibitor 853 as an ultraviolet-stabilized benzothiazole according to some embodiments. In FIG. 8B, G represents the rest of the photosensitizer (e.g., G is a hydrocarbyl or a substituted hydrocarbyl), examples of R' of benzothiazole 631 are provided above, and X can be hydrogen or a non-hydrogen (such as hydroxyl, amino, hydrocarbyl, thioether, and ether). As discussed above, the alkyne can be ortho, meta, or para to the group represented by G, such as a carbonyl group. FIG. 8B shows the alkyne group para to the group represented by G. In method 850, a Sonogashira cross-coupling is used to cross-couple a bromobenzothiazole 631 with an alkyne represented by alkyne 751 (e.g., alkyne 255, alkyne 355, alkyne 407, alkyne 457, and alkyne 503) and form the ultraviolet-stabilized corrosion inhibitor 853 as an ultraviolet-stabilized benzothiazole. The ultraviolet stabilized corrosion inhibitor 853 may be synthesized according to the prophetic Sonogashira cross-coupling described above.

Figure 9A:
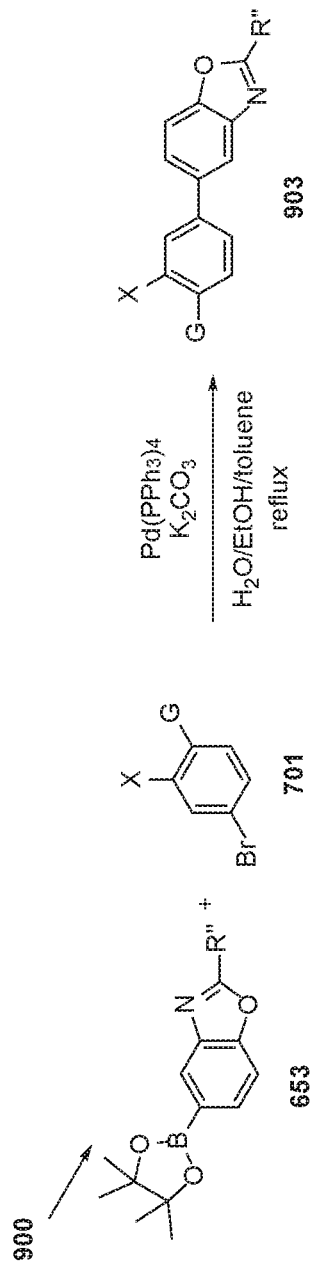
FIG. 9A is a chemical reaction diagram of a method 900 of forming an ultraviolet-stabilized corrosion inhibitor according to some embodiments.

FIG. 9A illustrates a method 900 of forming an ultraviolet-stabilized corrosion inhibitor 903 as an ultraviolet-stabilized benzoxazole according to some embodiments. In FIG. 9A, G represents the rest of the photosensitizer (e.g., G is a hydrocarbyl or a substituted hydrocarbyl), examples of R" of benzoxazole 653 are provided above, and X can be hydrogen or a non-hydrogen (such as hydroxyl, amino, hydrocarbyl, thioether, and ether). As discussed above, the bromide can be ortho, meta, or para to the group represented by G, such as a carbonyl group. FIG. 9A shows the bromide group para to the group represented by G. In method 900, a Suzuki cross-coupling is used to cross-couple a benzoxazole boronic ester 653 with a bromide represented by bromide 701 (e.g., bromide 205, bromide 305, bromide 405, bromide 455, bromide 501, and bromide 501a) and form the ultraviolet-stabilized corrosion inhibitor 903 as an ultraviolet-stabilized benzoxazole. The ultraviolet stabilized corrosion inhibitor 903 may be synthesized according to the prophetic Suzuki cross-coupling described above.

Figure 9B:
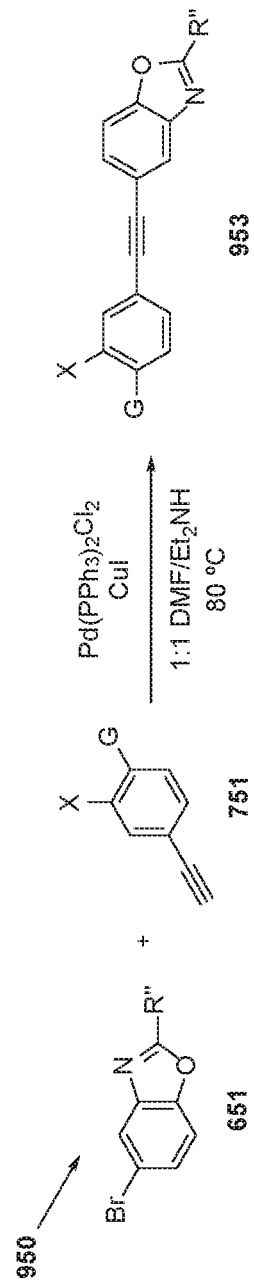
FIG. 9B is a chemical reaction diagram of a method 950 of forming an ultraviolet-stabilized corrosion inhibitor according to some embodiments.

FIG. 9B illustrates a method 950 of forming an ultraviolet-stabilized corrosion inhibitor 953 as an ultraviolet-stabilized benzoxazole according to some embodiments. In FIG. 9B, G represents the rest of the photosensitizer (e.g., G is a hydrocarbyl or a substituted hydrocarbyl), examples of R" of a benzoxazole 651 are provided above, and X can be hydrogen or a non-hydrogen (such as hydroxyl, amino, hydrocarbyl, thioether, and ether). As discussed above, the alkyne can be ortho, meta, or para to the group represented by G, such as a carbonyl group. FIG. 9B shows the alkyne group para to the group represented by G. In method 950, a Sonogashira cross-coupling is used to cross-couple the bromobenzoxazole 651 with an alkyne represented by alkyne 751 (e.g., alkyne 255, alkyne 355, alkyne 407, alkyne 457, and alkyne 503) and form the ultraviolet-stabilized corrosion inhibitor 953 as an ultraviolet-stabilized benzoxazole. The ultraviolet stabilized corrosion inhibitor 953 may be synthesized according to the prophetic Sonogashira cross-coupling described above.

Ultraviolet-stabilized corrosion inhibitors that can be made by this method include:

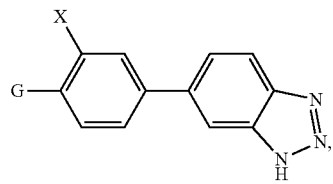

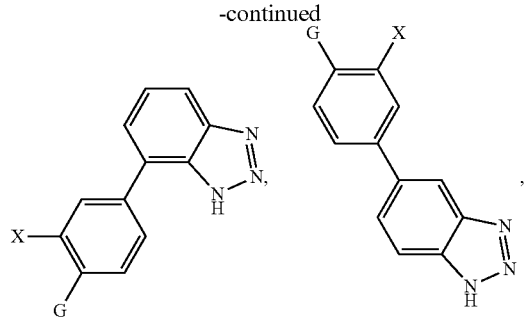

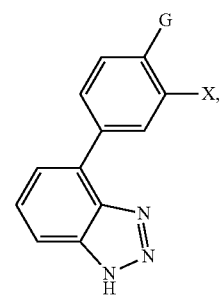

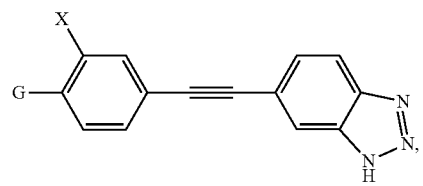

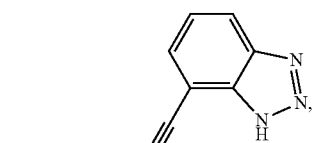

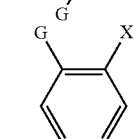

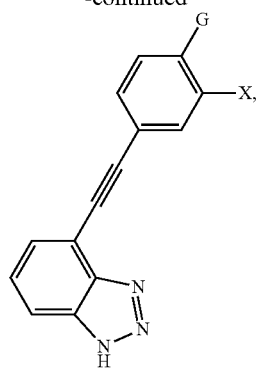
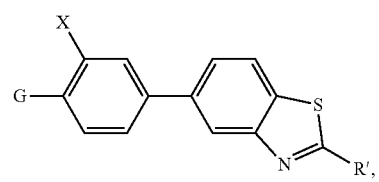
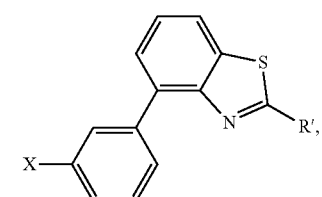
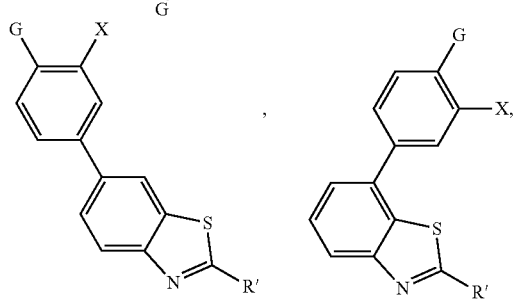
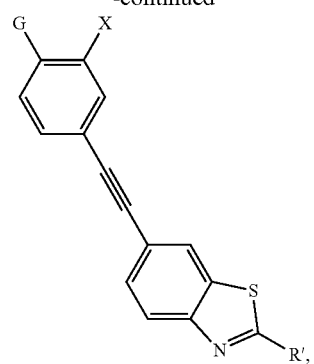
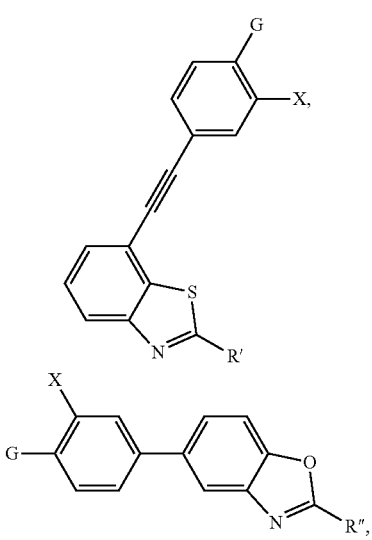
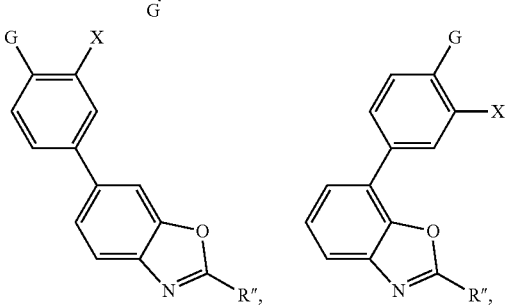
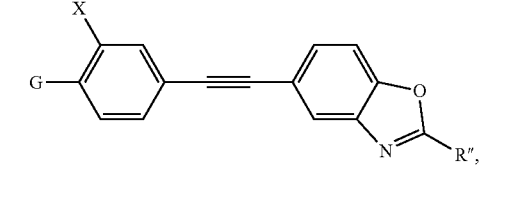

-continued

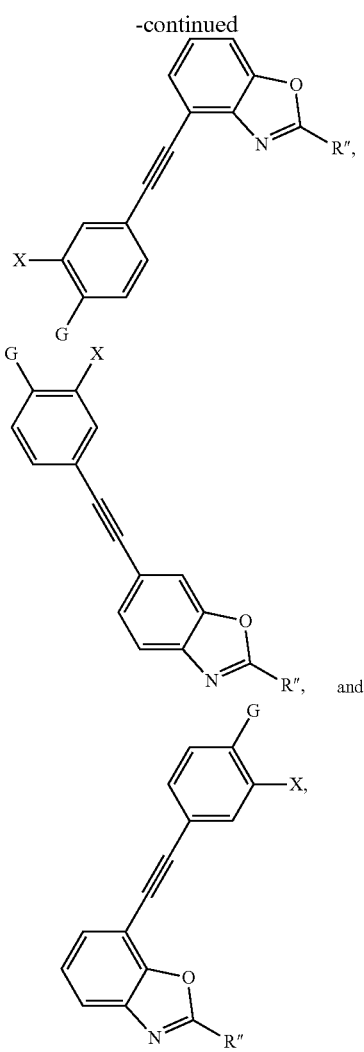

and wherein:

G is a hydrocarbyl or a substituted hydrocarbyl,

X is a hydrogen or a non-hydrogen (such as hydroxyl, amino, hydrocarbyl, thioether, and ether), R' is a hydrogen, a hydrocarbyl, an amino group, or a thioether group, and R" is a hydrogen, a hydrocarbyl, an alkoxy group, an aryl group, or a heteroaryl group.

Figure 10:
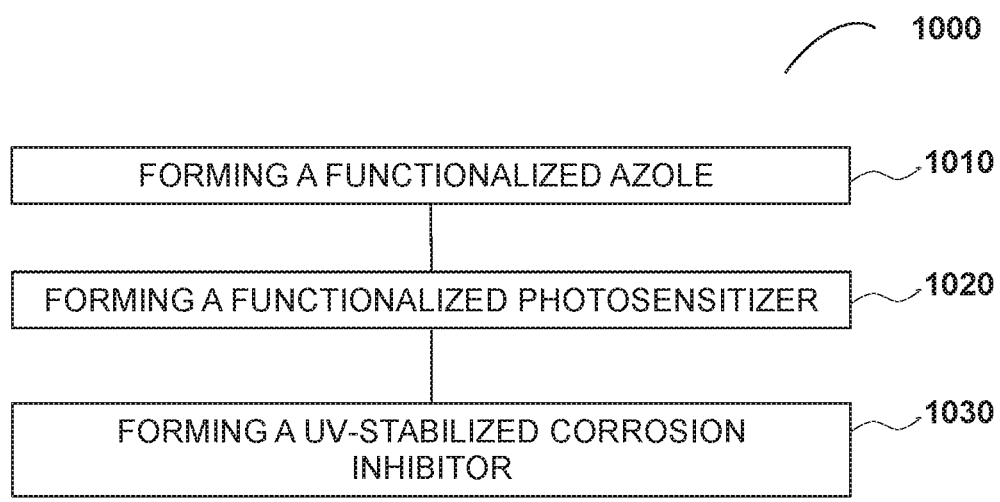
FIG. 10 is a block diagram illustrating a method 1000 of making an ultraviolet-stabilized corrosion inhibitor according to some embodiments.

FIG. 10 is a block diagram illustrating a method 1000 of making an ultraviolet-stabilized corrosion inhibitor according to some embodiments. The method 1000 includes forming a functionalized azole at operation 1010. The functionalized azole (e.g., an azole having a bromine or a boronic ester functional group) may be any azole described herein, for example 4-bromobenzotriazole 603 and benzotriazole boronic ester 607. The method 1000 further includes forming a functionalized photosensitizer at operation 1020. The functionalized photosensitizer (e.g., a photosensitizer having a bromine or an alkyne functional group) may be any photosensitizer described herein, for example bromide 701 and alkyne 751. The method 1000 further includes forming an ultraviolet-stabilized corrosion inhibitor (e.g., ultraviolet-stabilized corrosion inhibitors 703 and 753) by reacting the functionalized azole with the functionalized photosensitizer at operation 1030. The reaction may proceed via a cross-coupling reaction such as a Sonogashira cross-coupling reaction or a Suzuki cross-coupling reaction. It is contemplated that operation 1010 may be performed at the same time or after operation 1020.

The ultraviolet-stabilized corrosion inhibitors can be used in a variety of applications such as water cooling circuits and piping for oil and gas industries. In some embodiments, an article of manufacture comprises a material comprising an ultraviolet-stabilized corrosion inhibitor (e.g., ultraviolet-stabilized corrosion inhibitors 703 and 753). The ultraviolet stabilized corrosion inhibitor is a reaction product of an azole and a photosensitizer. In some embodiments, the article of manufacture further comprises one or more of an electronic component; a water cooling circuit; a copper material; and a copper alloy material.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present disclosure, other and further embodiments of the disclosure may be devised without departing from the basic scope thereof, and the scope thereof is determined by the claims that follow.

What is claimed is:

1. A method of forming an ultraviolet-stabilized corrosion inhibitor, comprising:

forming a functionalized azole, the functionalized azole comprising a bromine atom or a boronic ester;

forming a functionalized photosensitizer; and forming an ultraviolet-stabilized corrosion inhibitor by reacting the functionalized azole with the functionalized photosensitizer, wherein the ultraviolet-stabilized corrosion inhibitor is selected from the group consisting of

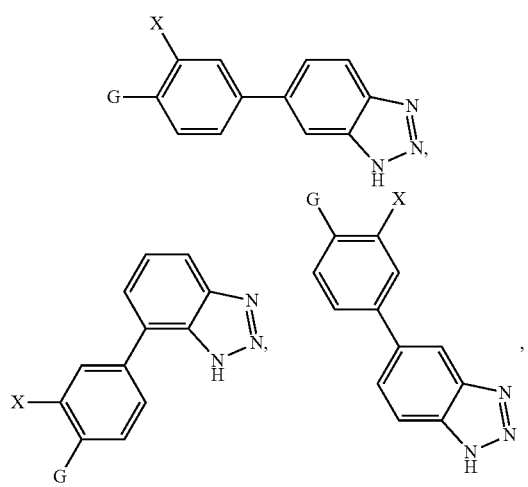

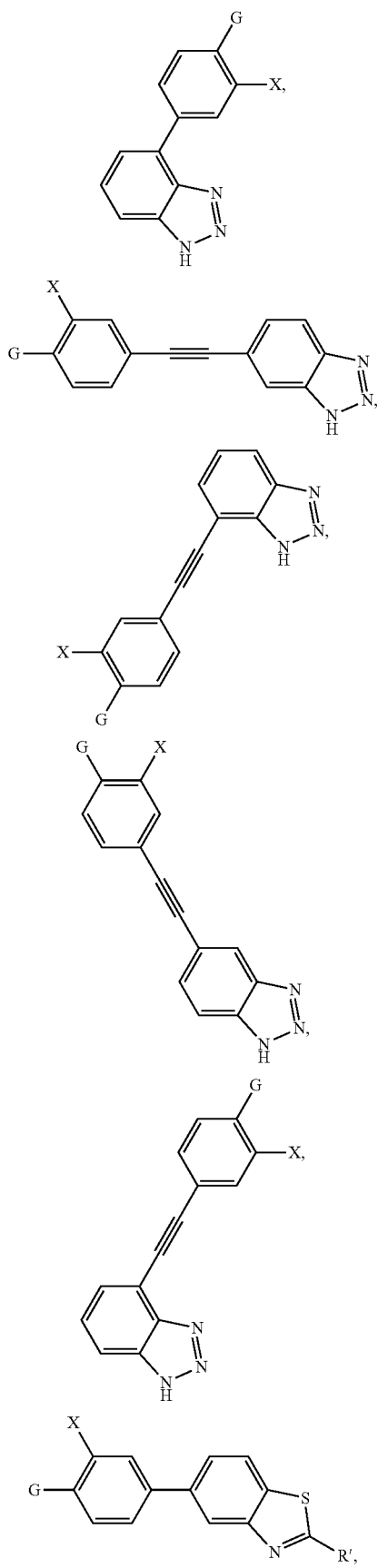
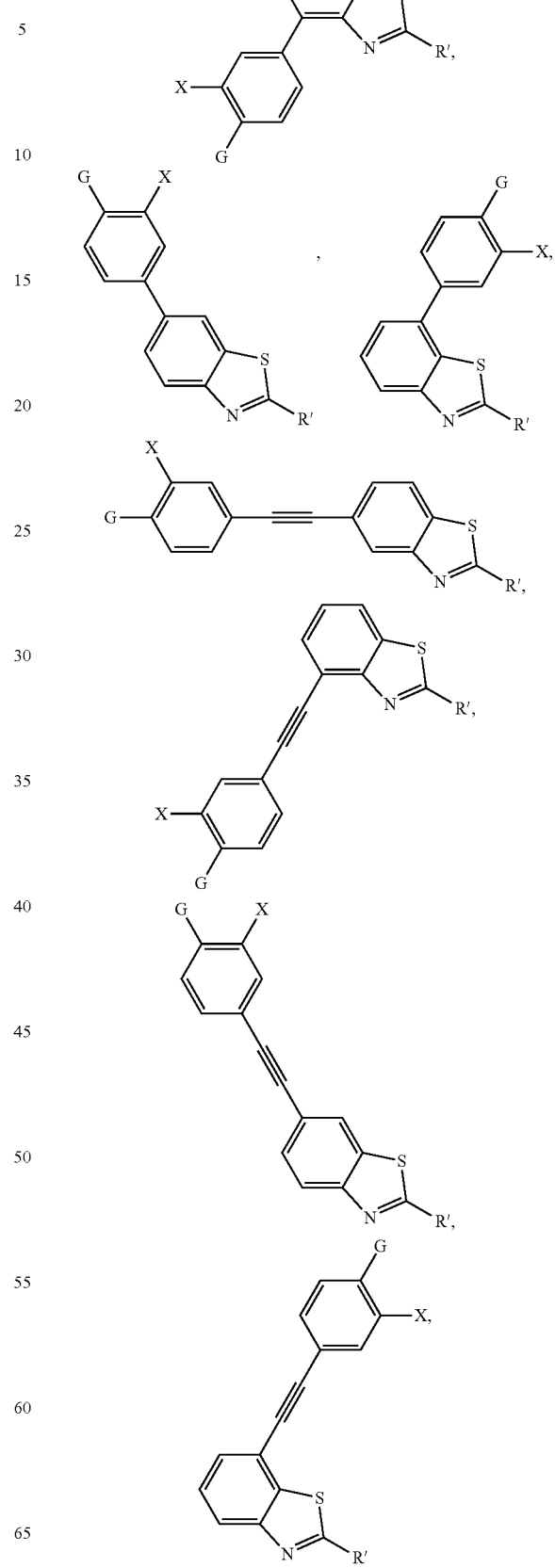

-continued

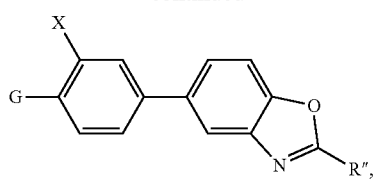

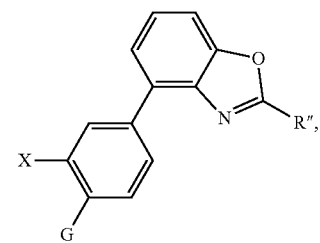

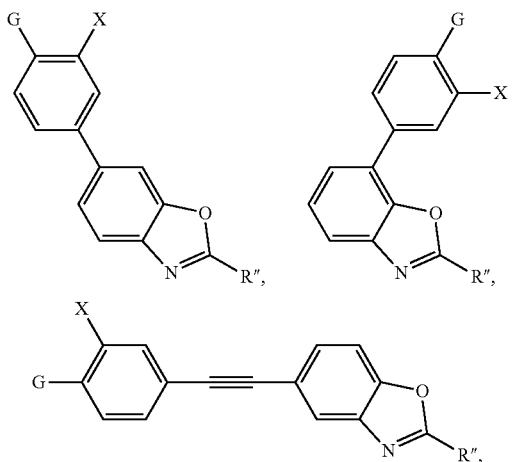

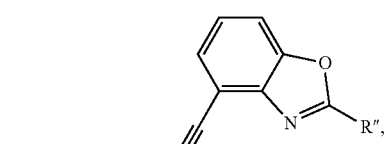

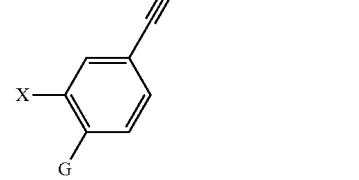

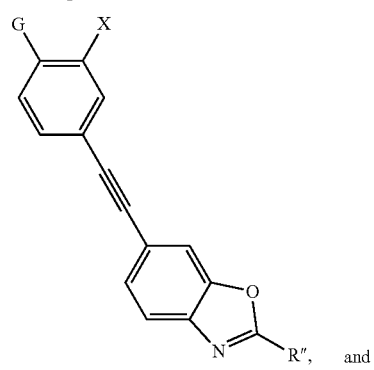 and

-continued

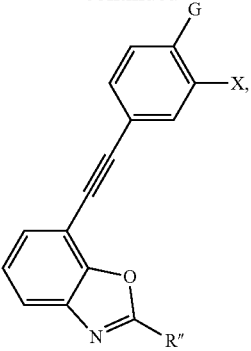

wherein:
G is a hydrocarbyl or a substituted hydrocarbyl,
X is a hydrogen, a hydroxyl group, an amino group, a hydrocarbyl, a thioether group, or an ether group,
R' is a hydrogen, a hydrocarbyl, an amino group, or a thioether group, and
R" is a hydrogen, a hydrocarbyl, an alkoxy group, an aryl group, or a heteroaryl group.

2. The method of claim 1, wherein the functionalized azole comprises a benzotriazole, a benzothiazole, a benzoxazole, or a derivative thereof.

3. The method of claim 1, wherein the functionalized azole comprises the bromine atom.

4. The method of claim 1, wherein the functionalized azole comprises the boronic ester.

5. The method of claim 1, wherein the functionalized photosensitizer comprises an avobenzone, an oxybenzone, an octisalate, an octocrylene, a homosalate, an octinoxate, or a derivative thereof.

6. The method of claim 1, wherein the functionalized photosensitizer comprises a bromine.

7. The method of claim 1, wherein the functionalized photosensitizer comprises an alkyne.

8. The method of claim 1, wherein the forming the ultraviolet-stabilized corrosion inhibitor comprises performing a palladium cross-coupling reaction.

9. A method of forming an ultraviolet-stabilized corrosion inhibitor, comprising:
forming a functionalized azole, the functionalized azole comprising a benzotriazole, a benzothiazole, a benzoxazole, or a derivative thereof, the functionalized azole further comprising a bromine atom or a boronic ester;
forming a functionalized photosensitizer; and
forming an ultraviolet-stabilized corrosion inhibitor by reacting the functionalized azole with the functionalized photosensitizer, wherein the ultraviolet-stabilized corrosion inhibitor is selected from the group consisting of

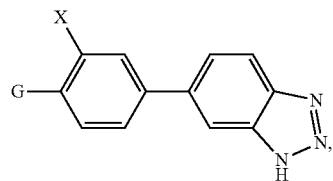

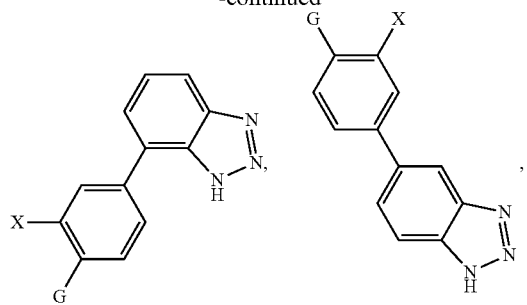
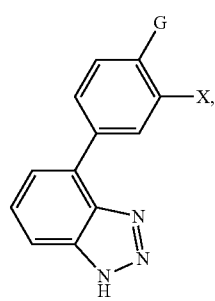
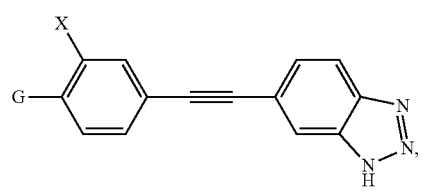
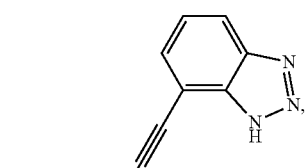
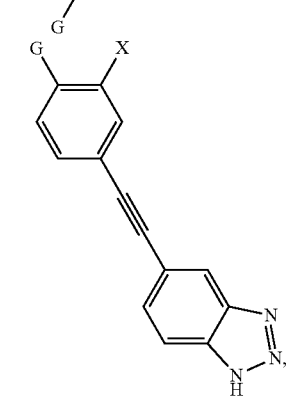
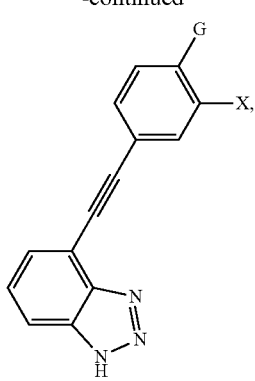
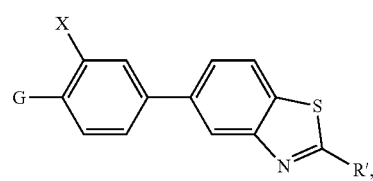
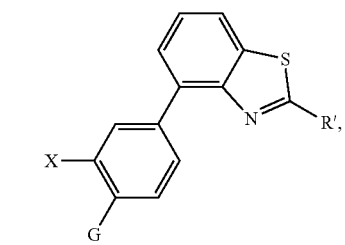
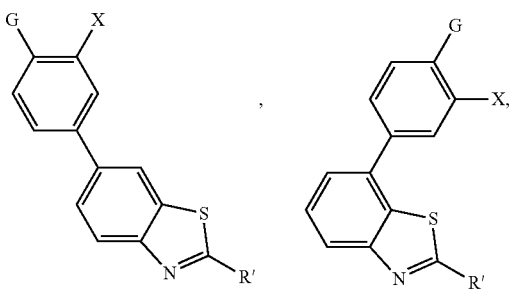
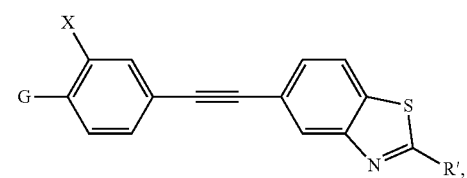
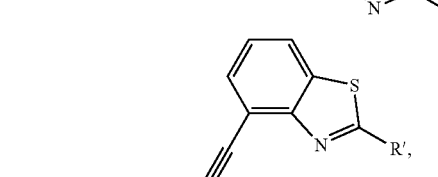
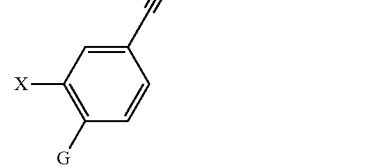

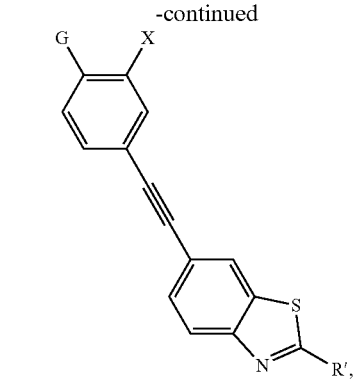
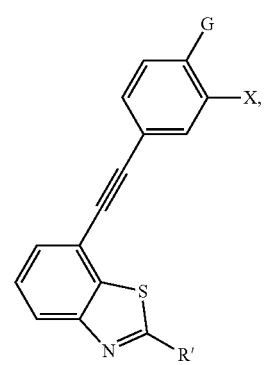
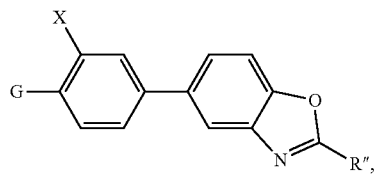
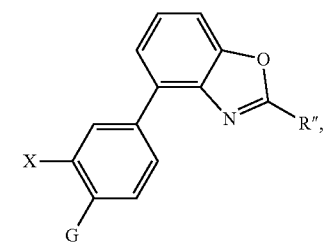
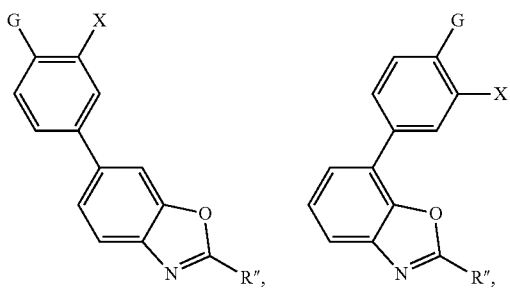
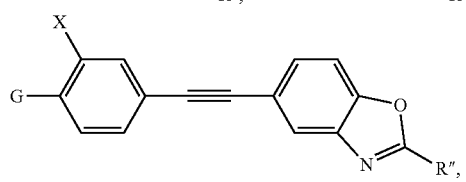

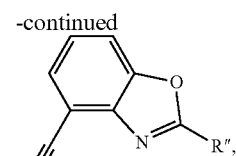
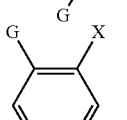
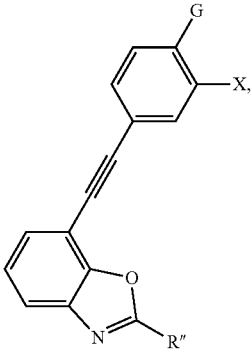

wherein:
G is a hydrocarbyl or a substituted hydrocarbyl,
X is a hydrogen, a hydroxyl group, an amino group, a hydrocarbyl, a thioether group, or an ether group,
R' is a hydrogen, a hydrocarbyl, an amino group, or a thioether group, and
R" is a hydrogen, a hydrocarbyl, an alkoxy group, an aryl group, or a heteroaryl group.

10. The method of claim 9, wherein the functionalized azole comprises the bromine atom.

11. The method of claim 9, wherein the functionalized azole comprises the boronic ester.

12. The method of claim 9, wherein the functionalized photosensitizer comprises an avobenzone, an oxybenzone, an octisalate, an octocrylene, a homosalate, an octinoxate, or a derivative thereof.

13. The method of claim 9, wherein the functionalized photosensitizer comprises a bromine.

14. The method of claim 9, wherein the functionalized photosensitizer comprises an alkyne.

15. The method of claim 9, wherein the forming the ultraviolet-stabilized corrosion inhibitor comprises performing a palladium cross-coupling reaction.

16. A method of forming an ultraviolet-stabilized corrosion inhibitor, comprising:
forming a functionalized azole, the functionalized azole comprising a benzotriazole, a benzothiazole, a benzoxazole, or a derivative thereof, the functionalized azole comprising a bromine atom or a boronic ester;

forming a functionalized photosensitizer; and forming an ultraviolet-stabilized corrosion inhibitor by reacting the functionalized azole with the functionalized photosensitizer, wherein the forming the ultraviolet-stabilized corrosion inhibitor comprises performing a palladium cross-coupling reaction, wherein the ultraviolet-stabilized corrosion inhibitor is selected from the group consisting of

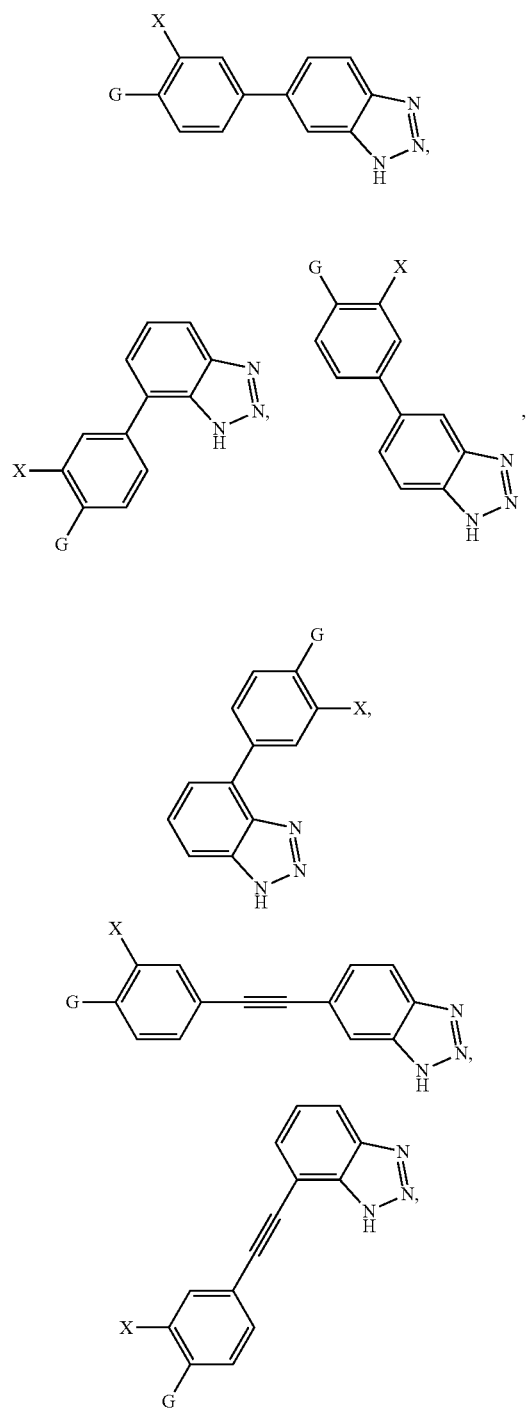

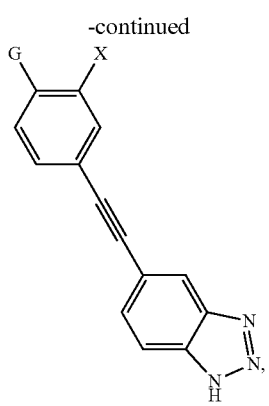

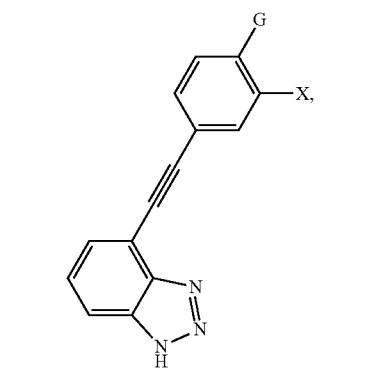

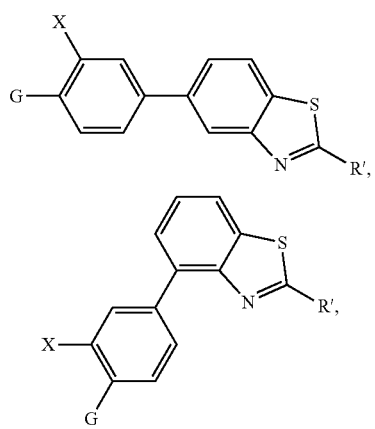

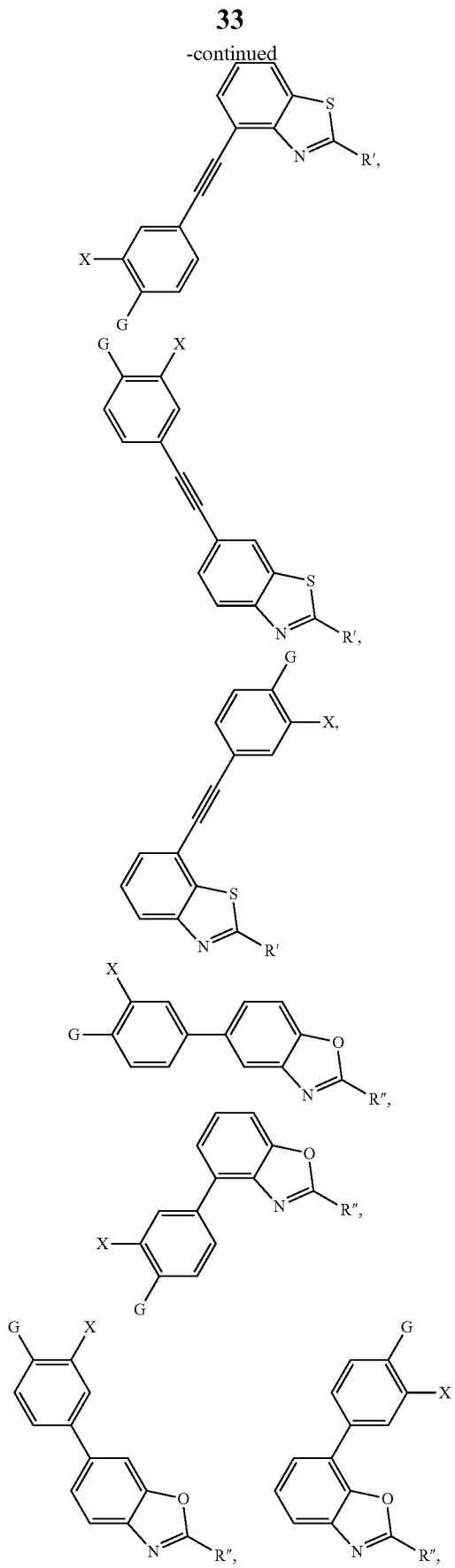

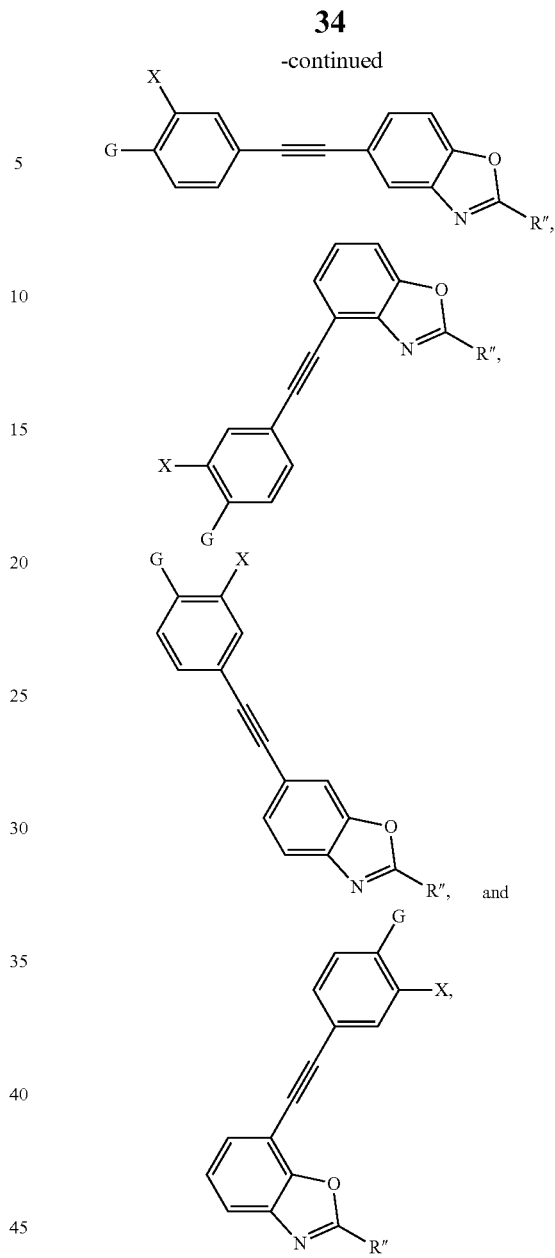

wherein:
G is a hydrocarbyl or a substituted hydrocarbyl,
X is a hydrogen, a hydroxyl group, an amino group, a hydrocarbyl, a thioether group, or an ether group,
R' is a hydrogen, a hydrocarbyl, an amino group, or a thioether group, and
R" is a hydrogen, a hydrocarbyl, an alkoxy group, an aryl group, or a heteroaryl group.

17. The method of claim 16, wherein the functionalized azole comprises the bromine atom.

18. The method of claim 16, wherein the functionalized azole comprises the boronic ester.

19. The method of claim 16, wherein the functionalized photosensitizer comprises an avobenzone, an oxybenzone, an octisalate, an octocrylene, a homosalate, an octinoxate, or a derivative thereof.

* * * * *